United States Patent
Kozuka et al.

(10) Patent No.: US 11,538,572 B2
(45) Date of Patent: Dec. 27, 2022

(54) CASE DISPLAY APPARATUS, CASE DISPLAYING METHOD, AND STORAGE MEDIUM BACKGROUND TO SEAMLESSLY PRESENT DIAGNOSTIC IMAGES CAPTURED AT DIFFERENT TIMES FOR COMPARATIVE READING

(71) Applicant: Panasonic Intellectual Property Management Co., Ltd., Osaka (JP)

(72) Inventors: Kazuki Kozuka, Osaka (JP); Kenji Kondo, Fukui (JP); Kazutoyo Takata, Fukui (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 0 days.

(21) Appl. No.: 16/654,066

(22) Filed: Oct. 16, 2019

(65) Prior Publication Data

US 2020/0046451 A1 Feb. 13, 2020

Related U.S. Application Data

(60) Division of application No. 14/997,540, filed on Jan. 17, 2016, now Pat. No. 10,492,883, which is a (Continued)

(30) Foreign Application Priority Data

Aug. 7, 2013 (JP) ................... 2013-164154
Jun. 23, 2014 (JP) ................... 2014-127893

(51) Int. Cl.
*A61B 6/03* (2006.01)
*A61B 6/00* (2006.01)
(Continued)

(52) U.S. Cl.
CPC ............ *G16H 30/20* (2018.01); *A61B 6/03* (2013.01); *A61B 6/032* (2013.01); *A61B 6/463* (2013.01);
(Continued)

(58) Field of Classification Search
CPC .......... G16H 30/20; A61B 6/03; A61B 6/463; A61B 6/032; A61B 6/469; A61B 90/37;
(Continued)

(56) References Cited

U.S. PATENT DOCUMENTS 9,323,402 B1* 4/2016 Fram ................. G06F 3/0482
2005/0259116 A1* 11/2005 Araoka .............. G16H 40/63
345/619
(Continued)

FOREIGN PATENT DOCUMENTS

JP 2002-253545 9/2002
JP 2004-173910 6/2004
(Continued)

OTHER PUBLICATIONS

International Search Report of PCT Application No. PCT/JP2014/003766 dated Sep. 22, 2014.
(Continued)

*Primary Examiner* — John T Repsher, III
(74) *Attorney, Agent, or Firm* — Wenderoth, Lind & Ponack, L.L.P.

(57) ABSTRACT

A user input obtainer receives an image movement instruction including identification information specifying a position shift or an image capture time shift to be performed and also including a displacement amount. When the identification information specifies the position shift, a slice position selector determines a tomographic image at a destination of the position shift based on the displacement amount from a set of tomographic images captured at the same time. On the
(Continued)

other hand, when the identification information specifies the image capture time shift, the image capture time selector determines a tomographic image at a destination of the shift based on the displacement amount from sets of tomographic images that are identical to each other in terms of a patient, an examination portion, and a modality. A displaying image obtainer reads out the determined tomographic image from an image storage device and gives it to a display information generator.

6 Claims, 21 Drawing Sheets

Related U.S. Application Data continuation of application No. PCT/JP2014/003766, filed on Jul. 16, 2014.

(51) Int. Cl.
*G06F 3/04842* (2022.01)
*G06F 3/04845* (2022.01)
*G06T 7/00* (2017.01)
*A61B 5/055* (2006.01)
*A61B 90/00* (2016.01)
*G06F 3/04847* (2022.01)
*G16H 30/20* (2018.01)

(52) U.S. Cl.
CPC .............. *A61B 6/469* (2013.01); *A61B 90/37* (2016.02); *G06F 3/04842* (2013.01); *G06F 3/04845* (2013.01); *G06F 3/04847* (2013.01); *G06T 7/0016* (2013.01); *A61B 5/055* (2013.01); *A61B 2090/374* (2016.02); *A61B 2090/378* (2016.02); *A61B 2090/3762* (2016.02); *A61B 2560/0487* (2013.01); *G06T 2200/24* (2013.01); *G06T 2207/10081* (2013.01); *G06T 2207/20108* (2013.01)

(58) Field of Classification Search
CPC ..... A61B 5/05; A61B 2090/378; A61B 5/055; G06F 3/04842; G06F 3/04845; G06F 3/04847; G06T 7/0016; G06T 2200/24; G06T 2207/10081; G06T 2207/20108
See application file for complete search history.

(56) References Cited

U.S. PATENT DOCUMENTS

| | | |
|---|---|---|
| 2006/0058624 A1 | 3/2006 | Kimura |
| 2007/0130515 A1 | 6/2007 | Maas |
| 2007/0150841 A1* | 6/2007 | Haras .................... G06F 3/0483 715/854 |
| 2009/0016491 A1 | 1/2009 | Li |
| 2009/0132279 A1* | 5/2009 | Yeluri .................... G16H 40/63 705/3 |
| 2011/0007061 A1 | 1/2011 | Ochiai et al. |
| 2011/0066627 A1* | 3/2011 | Seung ................. G06F 3/04883 707/758 |
| 2011/0234504 A1* | 9/2011 | Barnett ............... G06F 3/04883 345/173 |
| 2011/0255761 A1* | 10/2011 | O'Dell ....................... G06T 7/41 382/131 |
| 2011/0268336 A1* | 11/2011 | Dmitrieva ............. G06T 7/0014 382/131 |
| 2013/0093781 A1 | 4/2013 | Suzuki et al. |
| 2013/0205247 A1* | 8/2013 | Erhard .................. G06T 7/0012 715/781 |
| 2013/0227052 A1 | 8/2013 | Wenzel |
| 2014/0044421 A1 | 2/2014 | Sasaki |
| 2014/0071074 A1* | 3/2014 | Cousins ................ G06F 3/0412 345/173 |

FOREIGN PATENT DOCUMENTS

| | | |
|---|---|---|
| JP | 2005-224460 | 8/2005 |
| JP | 2006-095279 | 4/2006 |
| JP | 2006-277184 | 10/2006 |
| JP | 2007-517542 | 7/2007 |
| JP | 2009-018048 | 1/2009 |
| JP | 2011-017794 | 1/2011 |
| JP | 2012-230528 | 11/2012 |
| WO | 2011/122401 | 10/2011 |

OTHER PUBLICATIONS

Megumi Yamamoto et al., "Development of Computer-aided Diagnostic System for Detection of Lung Nodules in Three-dimensional Computed Tomography Images" Japanese Journal of Radiological Technology, vol. 62, No. 4, pp. 555-564, 2006 (English Abstract).

* cited by examiner

FIG. 5
| PATIENT ID | PATIENT NAME | EXAMINATION DATE | EXAMINATION TYPE | EXAMINATION PART | THUMBNAIL | REPORT |
|---|---|---|---|---|---|---|
| 0005 | AAAA | 02.14.2013 | CT | CHEST | 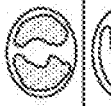 | NOT COMPLETED |
| 0004 | BBBB | 02.14.2013 | US | ABDOMEN |  | NOT COMPLETED |
| 0003 | CCCC | 02.13.2013 | X-RAY | HAND |  | NOT COMPLETED |
| 0002 | DDDD | 02.13.2013 | CT | CHEST | 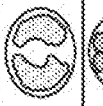 | NOT COMPLETED |
| 0001 | EEEE | 02.13.2013 | CT | CHEST |  | NOT COMPLETED |
| 0000 | FFFF | 02.12.2013 | MR | BRAIN |  | COMPLETED |

FIG. 6

| PATIENT ID | PATIENT NAME | EXAMINATION DATE | EXAMINATION TYPE | EXAMINATION PART | THUMBNAIL | REPORT |
|---|---|---|---|---|---|---|
| 0002 | DDDD | 02.13.2013 | CT | CHEST |  | NOT COMPLETED |
| 0002 | DDDD | 01.20.2013 | CT | CHEST |  | COMPLETED |
| 0002 | DDDD | 12.04.2012 | X-RAY | FOOT |  | COMPLETED |
| 0002 | DDDD | 08.05.2012 | CT | CHEST |  | COMPLETED |
| 0002 | DDDD | 04.13.2012 | CT | CHEST |  | COMPLETED |
| 0002 | DDDD | 01.10.2012 | CT | CHEST |  | COMPLETED |

CASE DISPLAY APPARATUS, CASE DISPLAYING METHOD, AND STORAGE MEDIUM BACKGROUND TO SEAMLESSLY PRESENT DIAGNOSTIC IMAGES CAPTURED AT DIFFERENT TIMES FOR COMPARATIVE READING

BACKGROUND

1. Technical Field

The present disclosure relates to a case display apparatus allowing it to seamlessly view diagnostic images captured at different times.

2. Description of the Related Art

In a known technique, a case display apparatus includes a storage unit that stores a time series of 2-dimensional or 3-dimensional first image data and second image data over a particular period of image capture time, a setting unit that sets a first portion of interest for the first image data and a second portion of interest, anatomically substantially identical to the first portion of interest, for the second image data at each phase in a plurality of phases in the particular period according to an instruction given by a user or via image processing, a correlating unit that correlates the set first portion of interest and the second portion of interest for each phase in the plurality of phases, and an image registration unit that makes an image registration between the first image data and the second image data according to a relative positional relationship between the correlated first portion of interest and the second portion of interest for each phase in the plurality of phase (see Japanese Unexamined Patent Application Publication No. 2011-177494).

In another known technique, an examination information displaying apparatus includes an acquisition unit that acquires examination information on a target person including a medical image captured by a medical imaging apparatus and attribute information attached to the examination information in terms of an examination date, an attribute indicating an examination item, or an attribute specific to the subject, and a display unit that displays the examination information acquired by the acquisition unit, wherein the examination information displaying apparatus further includes a generation unit that generates a history area defined by two axes including a first axis associated with one piece of attribute information of the plurality of pieces of attribute information and a second axis associated with attribute information different from the one piece of attribute information, and a display controller that controls displaying such that the examination information is displayed at corresponding coordinate positions of the first and second axes in the history area in the display screen of the display unit (see International Publication No. 2011/122401).

In diagnosis, doctors not only examine the 3-dimensional shape of a lesion or a disease state but also compare them with diagnostic images captured in the past. For example, by comparing a current image with a past image, it is determined whether the lesion tends to increase in size. This operation is called comparative reading. An increasingly large number of medical images are taken in digital form, and accordingly there is a need for a technique to efficiently perform comparative reading.

SUMMARY

One non-limiting and exemplary embodiment provides a case display apparatus capable of efficiently executing comparative reading.

In one general aspect, the techniques disclosed here feature that a case display apparatus includes a display information generator that generates display information displayed on a display device, a user input obtainer that, when the display information includes a first tomographic image, receives an image movement instruction including identification information and a displacement amount, the identification information specifying a slice position shift or an image capture time shift to be performed, a slice position selector that, when the identification information specifies that the slice position shift is to be performed, determines a second tomographic image at a destination of the slice position shift from a first tomographic image set including the first tomographic image, based on a position movement amount corresponding to the displacement amount, the first tomographic image set being a first plurality of tomographic images, an image capture time selector that, when the identification information specifies that the image capture time shift is to be performed, selects a third tomographic image from a second tomographic image set, the second tomographic image set being a second plurality of tomographic images, a target person of the first tomographic image and target persons of the second tomographic image set being identical, an examination portion captured in the first tomographic image and examination portions captured in the second tomographic image set being identical, a modality for the first tomographic image and modalities for the second tomographic image set being identical, and image capture times of the first tomographic image set and image capture times of the second tomographic image set being different, an image capture time of the third tomographic image being shifted from the image capture time of the first tomographic image based on the time movement amount corresponding to the displacement amount, a displaying image obtainer that reads out the second tomographic image or the third tomographic image from an image storage device, and that gives the read out tomographic image to the display information generator, a different-capture-time image obtainer that obtains a plurality of tomographic image sets from the image storage device, each of the plurality of tomographic image sets being a plurality of tomographic images, persons of the plurality of tomographic image sets being identical, examination portions captured in the plurality of tomographic image sets being identical, modalities for the plurality of tomographic image sets being identical, and image capture times of the plurality of tomographic image sets being different from each other, and an acute disease determiner that calculates a volume of a sick region for each tomographic image set in the plurality of tomographic image sets such that volume of the sick region has an one-to-one correspondence to the tomographic image set, calculates a rate of change with time in the sick region volume based on the calculated volumes and image capture times of the respective tomographic image sets, and determines that the sick region has become acutely worse when the rate of change with time in the sick region volume is equal to or greater than a predetermined threshold value, wherein acuteness information is added to one or more tomographic images stored in the image storage device, the acuteness information indicating that a sick region included in a tomographic image has become acutely worse, and wherein the display information generator generates the display information such that when a tomographic image received from the displaying image obtainer includes acuteness information added thereto, an indicator is added to the tomographic image so as to indicate that the tomographic image includes the acute sick region.

The case display apparatus according to the present disclosure allows a user to efficiently execute the comparative reading.

It should be noted that general or specific embodiments may be implemented as a system, a method, an integrated circuit, a computer program, a storage medium, or any selective combination thereof. An example usable as the storage medium is non-temporary storage medium such as a CD-ROM (Compact Disc-Read Only Memory).

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 5 is a diagram illustrating an example of a patient list;

FIG. 6 is a diagram illustrating an example of a past examination list;

DETAILED DESCRIPTION

Figure 1:
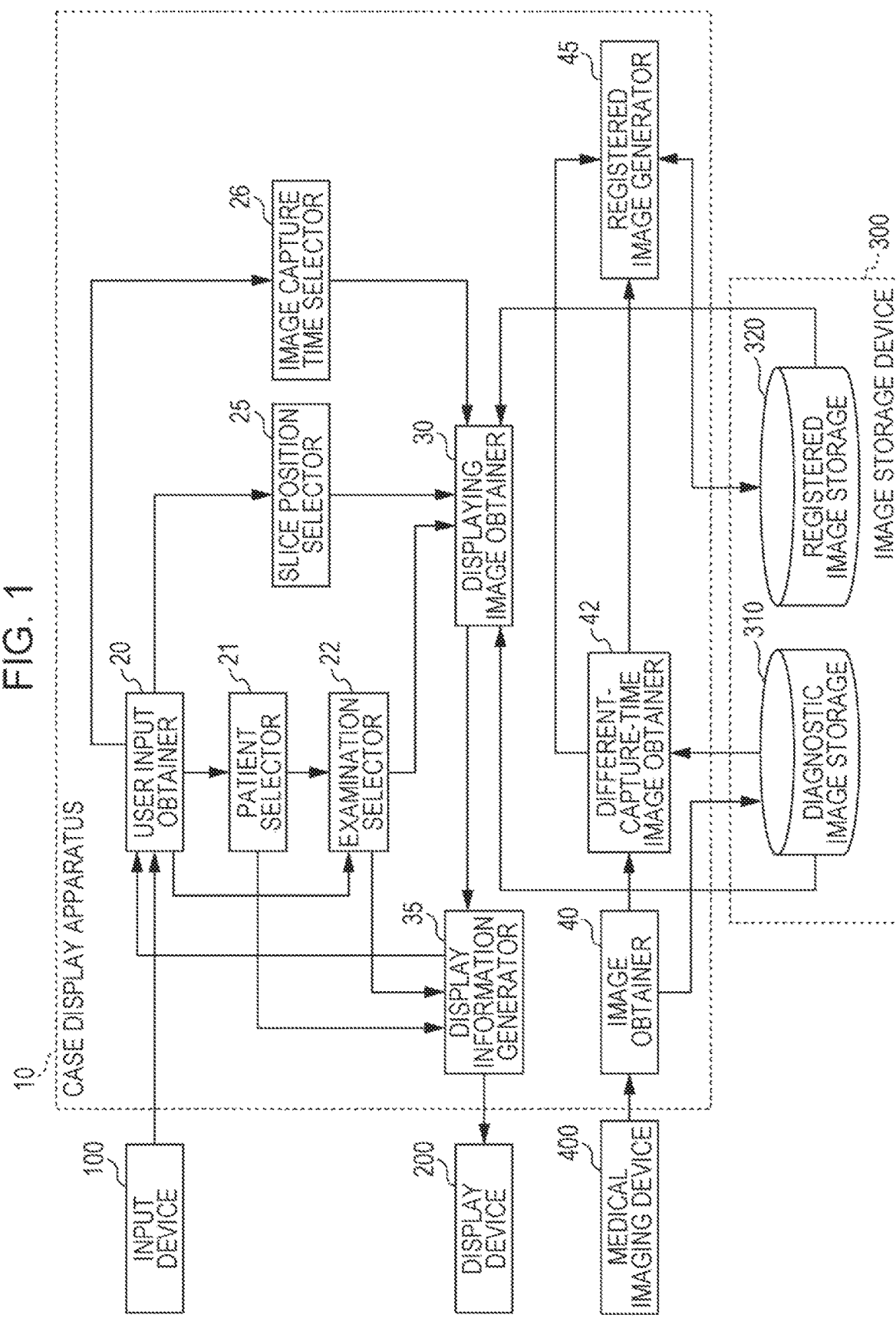
FIG. 1 is a block diagram illustrating a functional configuration of a case display apparatus according to a first embodiment.

Underlying Knowledge Forming Basis of the Present Disclosure

In a medical field, an increasingly great number of medical images of patients are captured in digital form. Medical image data is generated by a medical diagnostic imaging apparatus (a modality) such as CT (Computerized Tomography), MRI (Magnetic Resonance Imaging), an ultrasonic apparatus, or the like, and the medical image data is displayed on a display apparatus such as a monitor or the like when diagnosis is performed. A user or a doctor performs image reading to detect a lesion, recognize a disease state, observe a change with time, and the like. In particular, diagnosis using captured tomographic images makes it possible to recognize a 3-dimensional shape or disease state, and thus this diagnosis method is widely used by many medical organizations.

As a method of viewing tomographic images, it is known to use a case display apparatus that continuously displays slice positions in accordance with a displace input given by a user. For example, many case display apparatuses are available in market that are capable of changing a slice position in response to a mouse scroll operation. By viewing tomographic images while continuously changing the slice position according to the viewing method described above, it is possible to recognize a 3-dimensional shape of a lesion or a disease state.

In recent situations, there may be diagnostic images captured by a plurality of modalities for one patient, and there may be a plurality of image sets captured in each examination at different times. As an increasingly great number of medical images are captured in digital form, the number of patients and the number of images subjected to the comparative reading are accordingly increasing. In the comparative reading, users of case display apparatuses such as doctors are supposed to find out a necessary diagnostic image by browsing many examination lists. In such situations, doctors have to spend much time to perform a troublesome operation to find out a proper image. Thus, there is a need for a technique that allows it to perform comparative reading in a more efficient manner.

In view of the above, in a first aspect of the present disclosure, a case display apparatus includes a display information generator that generates display information displayed on a display device, a user input obtainer that, when the display information includes a first tomographic image, receives an image movement instruction including identification information and a displacement amount, the identification information specifying a slice position shift or an image capture time shift to be performed, a slice position selector that, when the identification information specifies that the slice position shift is to be performed, determines a second tomographic image at a destination of the slice position shift from a first tomographic image set including the first tomographic image, based on a position movement amount corresponding to the displacement amount, the first tomographic image set being a first plurality of tomographic images, an image capture time selector that, when the identification information specifies that the image capture time shift is to be performed, selects a third tomographic image from a second tomographic image set, the second tomographic image set being a second plurality of tomographic images, a target person of the first tomographic image and target persons of the second tomographic image set being identical, an examination portion captured in the first tomographic image and examination portions captured in the second tomographic image set being identical, a modality for the first tomographic image and modalities for the second tomographic image set being identical, and image capture times of the first tomographic image set and image capture times of the second tomographic image set being different, an image capture time of the third tomographic image being shifted from the image capture time of the first tomographic image based on the time movement amount corresponding to the displacement amount, a displaying image obtainer that reads out the second tomographic image or the third tomographic image from an image storage device, and that gives the read out tomographic image to the display information generator, a different-capture-time image obtainer that obtains a plurality of tomographic image sets from the image storage device, each of the plurality of tomographic image sets being a plurality of tomographic images, persons of the plurality of tomographic image sets being identical, examination portions captured in the plurality of tomographic image sets being identical, modalities for the plurality of tomographic image sets being identical, and image capture times of the plurality of tomographic image sets being different from each other, and an acute disease determiner that calculates a volume of a sick region for each tomographic image set in the plurality of tomographic image sets such that volume of the sick region has an one-to-one correspondence to the tomographic image set, calculates a rate of change with time in the sick region volume based on the calculated volumes and image capture times of the respective tomographic image sets, and determines that the sick region has become acutely worse when the rate of change with time in the sick region volume is equal to or greater than a predetermined threshold value, wherein acuteness information is added to one or more tomographic images stored in the image storage device, the acuteness information indicating that a sick region included in a tomographic image has become acutely worse, and wherein the display information generator generates the display information such that when a tomographic image received from the displaying image obtainer includes acuteness information added thereto, an indicator is added to the tomographic image so as to indicate that the tomographic image includes the acute sick region. Thus, it is possible to shift the image capture time of the displayed tomographic image in a similar manner as in a case where the slice position is shifted.

That is, in a case where there are many diagnostic images captured at different times, it is possible to seamlessly view a diagnostic image being currently used in a diagnosis and diagnostic images captured in the past, which makes it easier to perform a comparative reading in terms of a change in disease state and a size of a lesion among diagnostic images captured at different times.

In a second aspect of the present disclosure, a case display apparatus includes a display information generator that generates display information displayed on a display device, a user input obtainer that, when the display information includes a first tomographic image, receives an image movement instruction including identification information and a displacement amount, the identification information specifying a slice position shift or an image capture time shift to be performed, a slice position selector that, when the identification information specifies that the slice position shift is to be performed, determines a second tomographic image at a destination of the slice position shift from a first tomographic image set including the first tomographic image, based on a position movement amount corresponding to the displacement amount, the first tomographic image set being a first plurality of tomographic images, an image capture time selector that, when the identification information specifies that the image capture time shift is to be performed, selects a third tomographic image from a second tomographic image set, the second tomographic image set being a second plurality of tomographic images, a target person of the first tomographic image and target persons of the second tomographic image set being identical, an examination portion captured in the first tomographic image and examination portions captured in the second tomographic image set being identical, a modality for the first tomographic image and modalities for the second tomographic image set being identical, and image capture times of the first tomographic image set and image capture times of the second tomographic image set being different, an image capture time of the third tomographic image being shifted from the image capture time of the first tomographic image based on the time movement amount corresponding to the displacement amount, and a displaying image obtainer that reads out the second tomographic image or the third tomographic image from an image storage device, and that gives the read out tomographic image to the display information generator, wherein in a case where the user input obtainer does not receive a new image movement instruction within a predetermined period of time after an image capture time shift is performed on a tomographic image is performed, the displaying image obtainer and the display information generator control displaying such that the slice position of the displayed tomographic image is moved up and down in a tomographic image set including a tomographic image being currently displayed.

In the case display apparatus according to a third aspect based on the second aspect, the amount of the up-and-down movement of the slice position in the control of displaying is determined based on a size or a range of a lesion in the tomographic image set.

In the case display apparatus according to a fourth aspect based on the second aspect, the amount of the up-and-down movement of the slice position in the control of displaying is determined based on a size or a range of a lesion in a plurality of tomographic image sets that are identical to the tomographic image set including the tomographic image being currently displayed in terms of the target person, the examination portion, and the modality but that are different from each other in terms of the image capture time.

The case display apparatus according to a fifth aspect based on the second aspect further includes a viewing history recorder that records a viewing history including the past image movement instruction, wherein the amount of the up-and-down movement of the slice position in the control of displaying is determined based on the history in terms of the slice position shift described in the viewing history.

In a sixth aspect of the present disclosure, a case display apparatus, includes a display information generator that generates display information displayed on a display device, a user input obtainer that, when the display information includes a first tomographic image, receives an image movement instruction including identification information and a displacement amount, the identification information specifying a slice position shift or an image capture time shift to be performed, a slice position selector that, when the identification information specifies that the slice position shift is to be performed, determines a second tomographic image at a destination of the slice position shift from a first tomographic image set including the first tomographic image, based on a position movement amount corresponding to the displacement amount, the first tomographic image set being a first plurality of tomographic images, an image capture time selector that, when the identification information specifies that the image capture time shift is to be performed, selects a third tomographic image from a second tomographic image set, the second tomographic image set being a second plurality of tomographic images, a target person of the first tomographic image and target persons of the second tomographic image set being identical, an examination portion captured in the first tomographic image and examination portions captured in the second tomographic image set being identical, a modality for the first tomographic image and modalities for the second tomographic image set being identical, and image capture times of the first tomographic image set and image capture times of the second tomographic image set being different, an image capture time of the third tomographic image being shifted from the image capture time of the first tomographic image based on the time movement amount corresponding to the displacement amount, and a displaying image obtainer that reads out the second tomographic image or the third tomographic image from an image storage device, and that gives the read out tomographic image to the display information generator; wherein importance information is added to part of tomographic images stored in the image storage device to indicate that the part of the tomographic images are important images, and wherein when in a tomographic image set identical to the first tomographic image in terms of the target person, the examination portion, and the modality, there is a tomographic image added with the importance information between first tomographic image and the tomographic image determined by the image capture time selector, the displaying image obtainer reads out this tomographic image from the image storage device instead of the tomographic image determined by the image capture time selector.

The case display apparatus according to a seventh aspect based on the sixth aspect further includes a different-capture-time image obtainer that reads out, from the image storage device, a plurality of tomographic image sets that are identical to each other in terms of the target person, the examination portion, and the modality but that are different from each other in terms of the image capture time; an important image determiner that detects a rate of change with time in a lesion region by performing image processing for each tomographic image set in the plurality of tomographic image sets, and makes a determination such that if the rate of change with time is greater than a predetermined threshold value, a tomographic image including the lesion region is determined as an important image.

The case display apparatus according to an eighth aspect based on the sixth aspect further includes a viewing history recorder that records a viewing history of each tomographic image stored in the image storage device, and an important image determiner that determines an important image according to the viewing history.

The case display apparatus according to a ninth aspect based on the sixth aspect further includes an important image determiner that adds importance information to a tomographic image stored in the image storage device in accordance with an operation input by a user.

In a tenth aspect of the present disclosure, a method of displaying case data with a computer includes generating display information displayed on a display device, when the display information includes a first tomographic image, receiving an image movement instruction including identification information and a displacement amount, the identification information specifying a slice position shift or an image capture time shift to be performed, when the identification information specifies that the slice position shift is to be per formed, determining, based on the amount of the position shift corresponding to the displacement amount, a second tomographic image at a destination of the slice position shift from a first tomographic image set that is a first plurality of tomographic images including the first tomographic image, when the identification information specifies that the image capture time shift is to be performed, determining a third tomographic image from a second tomographic image set that is a second plurality of tomographic images that are identical to the first tomographic image in terms of a target person, an examination portion, and a modality but that are different from the first tomographic image set in terms of an image capture time, reading out the second tomographic image or the third tomographic image from an image storage device and newly generating display information including the read-out tomographic image, when a new image movement instruction is not received within a predetermined period of time after an image capture time shift is performed on a tomographic image, controlling displaying so as to move the slice position of the displayed tomographic image up and down in the tomographic image set including the tomographic image being currently displayed.

In an eleventh aspect of the present disclosure, there is provided a storage medium including a control program stored therein to control a device including a processor to execute a case displaying process including displaying case data, the storage medium being a computer-readable non-temporary storage medium, the case displaying process including generating display information displayed on a display device, when the display information includes a first tomographic image, receiving an image movement instruction including identification information and a displacement amount, the identification information specifying a slice position shift or an image capture time shift to be performed, when the identification information specifies that the slice position shift is to be performed, determining, based on the displacement amount, a second tomographic image at a destination of the slice position shift from a first tomographic image set that is a first plurality of tomographic images including the first tomographic image, when the identification information specifies that the image capture time shift is to be performed, determining a third tomographic image from a second tomographic image set that is a second plurality of tomographic images that are identical to the first tomographic image in terms of a target person, an examination portion, and a modality but that are different from the first tomographic image set in terms of an image capture time, the image capture time of the third tomographic image being shifted from the image capture time of the first tomographic image based on the amount of the image capture time shift corresponding to the displacement amount, reading out the second tomographic image or the third tomographic image from an image storage device and newly generating display information including the read-out tomographic image, when a new image movement instruction is not received within a predetermined period of time after an image capture time shift is performed on a tomographic image, controlling displaying so as to move the slice position of the displayed tomographic image up and down in the tomographic image set including the tomographic image being currently displayed.

In a twelfth aspect of the present disclosure, a method of displaying case data with a computer includes generating display information displayed on a display device, when the display information includes a first tomographic image, receiving an image movement instruction including identification information and a displacement amount, the identification information specifying a slice position shift or an image capture time shift to be performed, when the identification information specifies that the slice position shift is to be per formed, determining, based on the amount of the position shift corresponding to the displacement amount, a second tomographic image at a destination of the slice position shift from a first tomographic image set that is a first plurality of tomographic images including the first tomographic image, when the identification information specifies that the image capture time shift is to be performed, determining a third tomographic image from a second tomographic image set that is a second plurality of tomographic images that are identical to the first tomographic image in terms of a target person, an examination portion, and a modality but that are different from the first tomographic image set in terms of an image capture time, the image capture time of the third tomographic image being shifted from the image capture time of the first tomographic image based on the amount of the image capture time shift corresponding to the displacement amount, reading out the second tomographic image or the third tomographic image from an image storage device and newly generating display information including the read-out tomographic image, wherein importance information is added to part of tomographic images stored in the image storage device to indicate that the part of the tomographic images are important images, and wherein when in a tomographic image set identical to the first tomographic image in terms of the target person, the examination portion, and the modality, there is a tomographic image added with the importance information between first tomographic image and the determines second tomographic image or second tomographic image, this tomographic image added with the importance information is read out from the image storage device instead of the determined second tomographic image or third tomographic image.

In a thirteenth aspect of the present disclosure, there is provided a storage medium including a control program stored therein to control a device including a processor to execute a case displaying process including displaying case data, the storage medium being a computer-readable non-temporary storage medium, the case displaying process including generating display information displayed on a display device, when the display information includes a first tomographic image, receiving an image movement instruction including identification information and a displacement amount, the identification information specifying a slice position shift or an image capture time shift to be performed, when the identification information specifies that the slice position shift is to be per formed, determining, based on the amount of the position shift corresponding to the displacement amount, a second tomographic image at a destination of the slice position shift from a first tomographic image set that is a first plurality of tomographic images including the first tomographic image, when the identification information specifies that the image capture time shift is to be performed, determining a third tomographic image from a second tomographic image set that is a second plurality of tomographic images that are identical to the first tomographic image in terms of a target person, an examination portion, and a modality but that are different from the first tomographic image set in terms of an image capture time, the image capture time of the third tomographic image being shifted from the image capture time of the first tomographic image based on the amount of the image capture time shift corresponding to the displacement amount, reading out the second tomographic image or the third tomographic image from an image storage device and newly generating display information including the read-out tomographic image, wherein importance information is added to part of tomographic images stored in the image storage device to indicate that the part of the tomographic images are important images, and wherein when in a tomographic image set identical to the first tomographic image in terms of the target person, the examination portion, and the modality, there is a tomographic image added with the importance information between first tomographic image and the determines second tomographic image or second tomographic image, this tomographic image added with the importance information is read out from the image storage device instead of the determined second tomographic image or third tomographic image.

In the present specification, a "tomographic image set" refers to a set of sequential tomographic images (slice images) captured for an examination portion of a patient (a target person) at the same time by a modality. In a case where tomographic images are captured within a predetermined period (for example, 60 minutes), it may be regarded that these tomographic images are captured at the same time. For example, in a case where in a period from 8:30 to 9:15 on May 1, 2012, 40 diagnostic images were captured by the same modality for the same examination portion of the same patient, the image capture time of each of the 40 tomographic images may be set to 8:30 on May 1, 2012. In this case, the diagnostic images may be tomographic images. The "slice position shift" refers to moving of a slice position of a displayed tomographic image in a tomographic image set. The "image capture time shift" refers to moving of an image capture time of a displayed tomographic image between different tomographic image sets that are identical in terms of a patient, an examination portion, and a modality but that are different from each other in terms of the image capture time.

First Embodiment

Configuration

FIG. 1 is a block diagram illustrating a functional configuration of a case display apparatus according to a first embodiment. In FIG. 1, the case display apparatus 10 includes a user input obtainer 20, a patient selector 21, an examination selector 22, a slice position selector 25, an image capture time selector 26, a displaying image obtainer 30, a display information generator 35, a captured image obtainer 40, a different-capture-time image obtainer 42, and a registered image generator 45. The case display apparatus 10 is connected to an input device 100, a display device 200, an image storage device 300, and a medical imaging device 400 so as to form a case displaying system.

Figure 2:
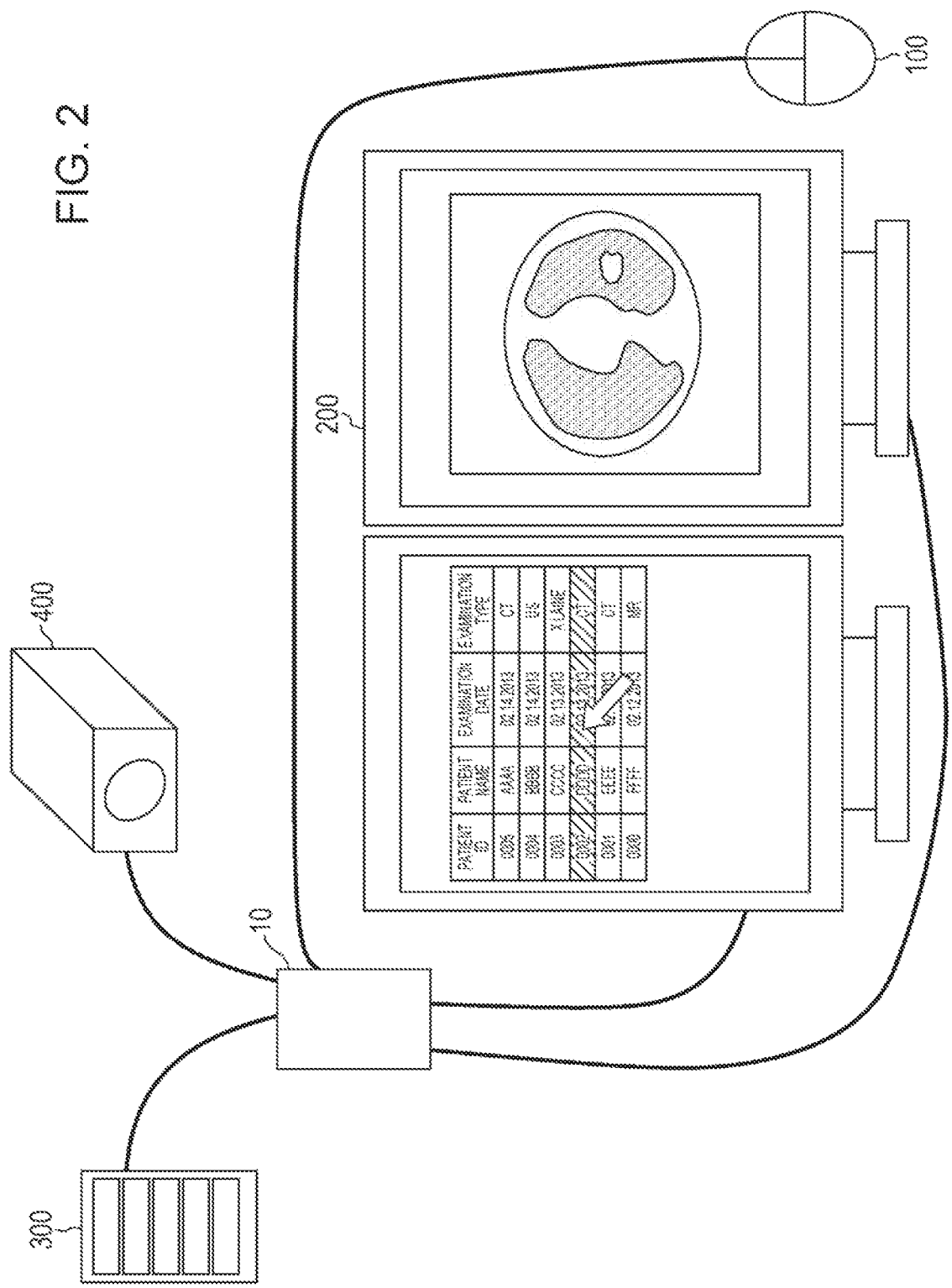
FIG. 2 is a diagram illustrating an example of a manner in which a case displaying system is used.

FIG. 2 illustrates an example of a manner in which the case displaying system is used. As illustrated in FIG. 2, the case displaying system is used by a user or a doctor in an image reading operation. In the case display apparatus 10, in response to an operation of the input device 100 (the mouse in FIG. 2), a medical image is read out from the image storage device 300 and displayed on the display device 200. An image captured by the medical imaging device 400 is stored in the image storage device 300.

Figure 3:
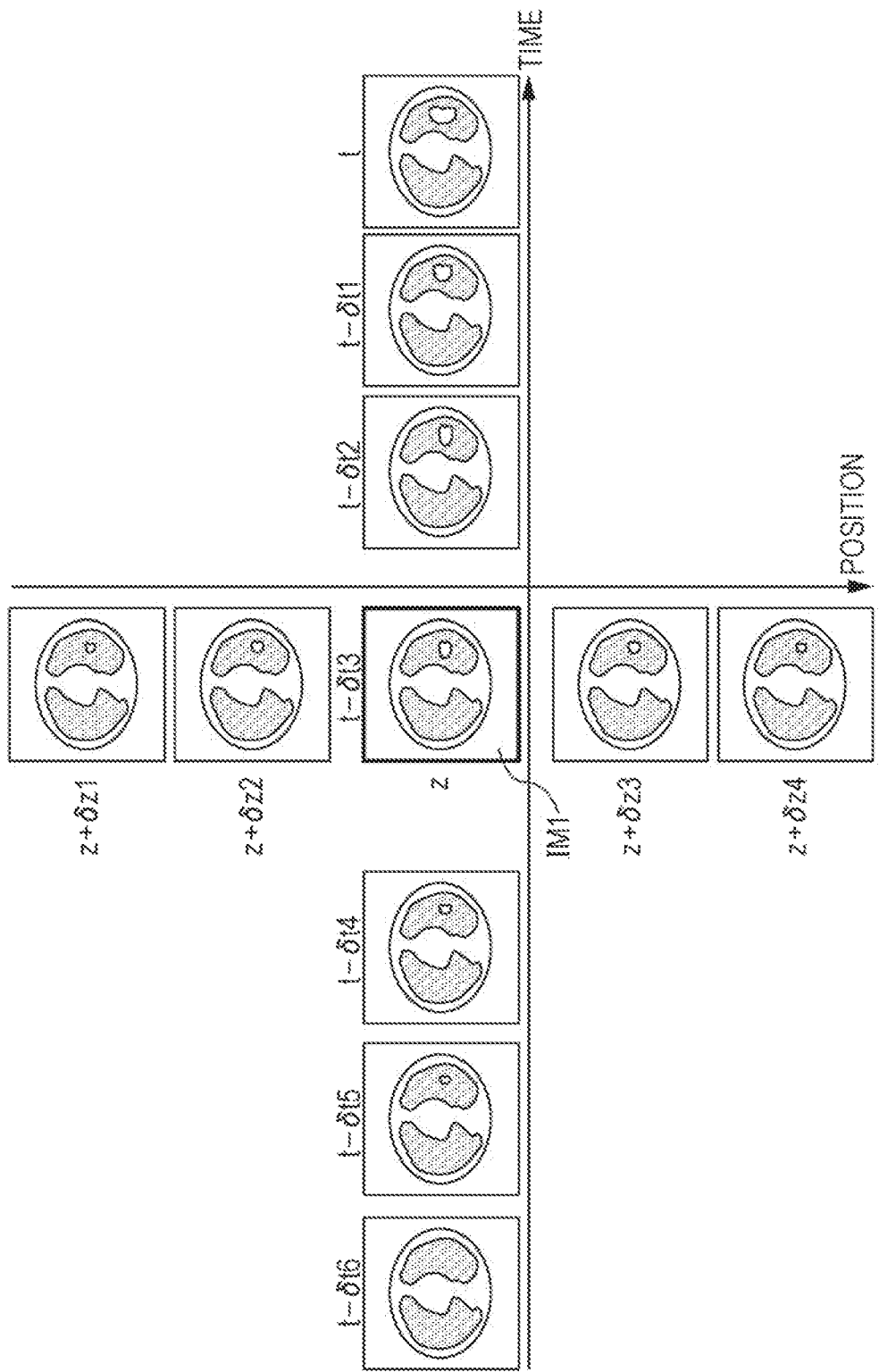
FIG. 3 is a diagram conceptually illustrating a manner in which tomographic images are displayed according to the first embodiment.

FIG. 3 is a diagram conceptually illustrating a manner in which tomographic images are displayed according to the present embodiment. In the present embodiment, the tomographic image IM1 being currently displayed can be subjected not only to changing of a slice position but also changing of an image capture time in response to an operation of the input device 100. This makes it possible for a user to change the tomographic image continuously in terms of image capture time, which makes it easy to recognize a change with time in lesion. Thus it becomes possible to easily perform comparative reading.

Each constituent element in the configuration shown in FIG. 1 is described below.

The input device 100 is a device used by a user to input a patient selection command, an examination selection command, a slice image move command, and the like. Examples usable as the input device 100 includes a mouse, a keyboard, a touch panel, and the like. Examples of information input by the input device 100 include a mouse click position, a scroll amount, a value input via keyboard, a touch position, and the like.

The user input obtainer 20 obtains input information based on the operation of the input device 100 performed by a user. The user input obtainer 20 outputs the input information or information based on the input information to one of the patient selector 21, the examination selector 22, the slice position selector 25, and the image capture time selector 26, depending on the content of the obtained input information.

For example, the user input obtainer 20 receives from the display information generator 35 information associated with display information displayed on the display device 200. This information includes information associated with a display content (for example, a list or an image displayed in a window) and information associated with a displaying position (for example, a displaying position in a window). When a patient list is displayed on the display device 200, if a position on the screen is specified using the input device 100, the user input obtainer 20 outputs to the patient selector 21 a patient ID of a patient (information identifying the patient) indicated at the specified position. In another situation, for example, when an examination list of a patient is displayed on the display device 200, if a position on the screen is specified using the input device 100, the user input obtainer 20 outputs to the examination selector 22 an examination ID of an examination indicated at the specified position. Herein, the examination ID is information uniquely assigned to an examination. For example, a Series Instance UID of DICOM information is an examination ID.

Note that the examination ID may include information identifying a medical diagnostic imaging apparatus (modality) and information identifying an examination portion.

When the patient selector 21 receives a patient ID from the user input obtainer 20, the patient selector 21 sends information associated with this patient ID, such as an examination list, to the display information generator 35. Furthermore, the patient selector 21 sends the patient ID to the examination selector 22. The user input obtainer may store the patient ID.

When the examination selector 22 receives the examination ID from the user input obtainer 20, the examination selector 22 outputs information, associated with the received examination ID described in examination information of the patient ID sent from the patient selector 21, to the displaying image obtainer 30 and the display information generator 35. The user input obtainer 20 may store this examination ID.

When a tomographic image is displayed on the display device 200, the user input obtainer 20 may receive an image movement instruction as input information given using the input device 100. The image movement instruction includes identification information specifying whether a slice position of the tomographic image is to be moved or an image capture time of the tomographic image is to be changed. Furthermore, the image movement instruction also includes a displacement amount specified by a user operation. In a case where the identification information specifies that the slice position shift is to be performed, the user input obtainer 20 outputs the image movement instruction to the slice position selector 25. On the other hand, in a case where the identification information specifies that the image capture time shift is to be performed, the user input obtainer 20 outputs the image movement instruction to the image capture time selector 26.

For example, in a case where the input device 100 is a mouse, the identification information may be given when the mouse is moved in a particular direction (for example, a vertical direction or a horizontal direction). Furthermore, a displacement amount may be specified by a mouse scroll amount, an amount of mouse dragging, or the like. For example, in a case where the input device 100 is a touch panel, the identification information may be given when a finger is moved in a particular direction (for example, a vertical direction or a horizontal direction) while being in contact with the touch panel. In this case, a displacement amount may be specified by a distance of a movement of a finger during the touch operation. Note that the methods of inputting identification information and the displacement amount in the image movement instruction using the input device 100 are not limited to those described above.

When the slice position selector 25 receives the image movement instruction from the user input obtainer 20, the slice position selector 25 determines a position to which the tomographic image is to be moved, and further determines the image ID of the tomographic image to be displayed. That is, when the identification information specifies that the slice position shift is to be performed, a tomographic image at a destination of the slice position shift is determined, based on the displacement amount, from a tomographic image set including the tomographic image being currently displayed on the display device 200 (that is, from a set of tomographic images captured at the same time as the tomographic image being currently displayed was captured). More specifically, for example, the displacement amount is converted to an amount of slice position shift and this amount of slice position shift is added to the slice position of the image being currently displayed, and finally an image ID is determined for a tomographic image located at the resultant slice position. The determined image ID is output to the displaying image obtainer 30. Thus it becomes possible to perform the movement in the vertical direction shown in FIG. 3. Note that the conversion relationship between the displacement amount and the amount of the position shift may be set in advance or may be determined by a user. Note that the image ID is information uniquely identifying each image. An example of the image ID is an SOP Instance UID of DICOM information.

When the image capture time selector 26 receives the image movement instruction from the user input obtainer 20, the slice position selector 25 determines the image capture time of the tomographic image to be obtained as a result of the image capture time shift, and determines the image ID of the tomographic image to be displayed. That is, in a case where the identification information specifies that the image capture time shift is to be performed, the tomographic image obtained as a result of the image capture time shift is determined according to the given displacement amount from tomographic image sets that are identical to the tomographic image being currently displayed on the display device 200 in terms of the patient, the examination portion, and the modality but that are different from each other in terms of the image capture time. More specifically, for example, the displacement amount is converted to an amount of the image capture time shift, and an image ID is determined for a tomographic image obtained by shifting the image capture time by the determined amount. The determined image ID is output to the displaying image obtainer 30. Thus it becomes possible to perform the movement in the horizontal direction shown in FIG. 3. Note that the conversion relationship between the displacement amount and the amount of the image capture time shift may be set in advance or may be determined by a user.

Note that the patient, that is, the target person, of the tomographic image being displayed on the display device may be determined based on the patient ID stored in the user input obtainer 20. The modality and the examination portion of the tomographic image being currently displayed on the display device may be determined based on the examination ID stored in the user input obtainer 20.

In a case where the identification information specifies that the image capture time shift is to be performed, tomographic image sets that are identical to the tomographic image being currently displayed on the display device 200 in terms of the patient, the examination portion, and the modality may be given by tomographic image sets that are identical in terms of the patient ID identifying the patient stored in the user input obtainer 20, information included in the examination ID and identifying the medical diagnostic imaging apparatus (the modality), and information identifying the examination portion.

When the displaying image obtainer 30 receives an examination ID from the examination selector 22, to the displaying image obtainer 30 reads out, from the image storage device 300, one of images captured in the examination identified by the received examination ID. On the other hand, when the displaying image obtainer 30 receives an image ID from the slice position selector 25 or the image capture time selector 26, the displaying image obtainer 30 reads out a tomographic image identified by the received image ID from the image storage device 300. Note that it is assumed herein that the tomographic image is read out from a registered image storage unit 320 described later. However, alternatively, the tomographic image may be read out from a diagnostic image storage unit 310 in which original diagnostic images are stored. The displaying image obtainer 30 outputs the read-out tomographic image to the display information generator 35.

The display information generator 35 acquires information associated with the patient ID from the patient selector 21, information associated with the examination ID from the examination selector 22, and the tomographic image from the displaying image obtainer 30. The display information generator 35 then generates display information using the acquired information and the tomographic image, and outputs the resultant display information to the display device 200.

The display device 200 may be a liquid crystal monitor, a tablet, or the like, that displays the display information received from the display information generator 35.

The image storage device 300 is a storage device that stores captured diagnostic images. In the configuration shown in FIG. 1, the image storage device 300 includes the diagnostic image storage unit 310 and the registered image storage unit 320. The diagnostic image storage unit 310 stores original captured diagnostic images, and the registered image storage unit 320 stores diagnostic images obtained as a result of an organ position registration over a plurality of times. Use of the registered images makes it possible to achieve high stability in terms of the organ position in displayed tomographic images when the image captured time thereof is continuously changed. That is, it is possible to achieve displayed images that are easy to view.

The medical imaging device 400 captures a diagnostic image of various types such a CT image, an MRI image, or the like. When an examination is performed, an operator of the medical imaging device 400 may input information identifying a patient, that is, a target person (patient identification information), information identifying an examination portion (examination portion identification information), and/or the like to the medical imaging device 400.

The captured image obtainer 40 acquires a diagnostic image captured by the medical imaging device 400. The medical imaging device 400 may add additional information to the diagnostic image wherein the additional information may be the patient identification information that is information identifying the patient, i.e., the target person, the examination portion identification information identifying the examination portion, the modality identification information identifying the modality, captured image identification information including information identifying an image capture time, and/or the like. The medical imaging device 400 may add information identifying each diagnostic image to the diagnostic image. The captured image obtainer 40 may add the same identification information to tomographic images that are identical to each other in terms of the patient identification information, the examination portion identification information, the modality identification information, and the image capture time. The acquired diagnostic image is stored in the diagnostic image storage unit 310 of the image storage device 300.

The different-capture-time image obtainer 42 acquires, from the diagnostic image storage unit 310, tomographic image sets that are identical to each other in terms of the patient, the examination portion, and the modality but that are different from each other in terms of the image capture time. In this acquisition process, the tomographic image set acquired by the captured image obtainer 40 may be included in the tomographic image sets. To determine tomographic image sets that are identical to each other in terms of the patient, the examination portion, and the modality but that are different from each other in terms of the image capture time, the captured image identification information may be referred to.

The registered image generator 45 perform a shape registration on an organ among diagnostic images over a plurality of times. That is, the registered image generator 45 acquires tomographic image sets that are different from each other in terms of the image capture time from the different-capture-time image obtainer 42, and performs the organ position registration among these tomographic image sets. The tomographic images obtained as a result of the image registration are stored in the registered image storage unit 320.

Operation

Figure 4:
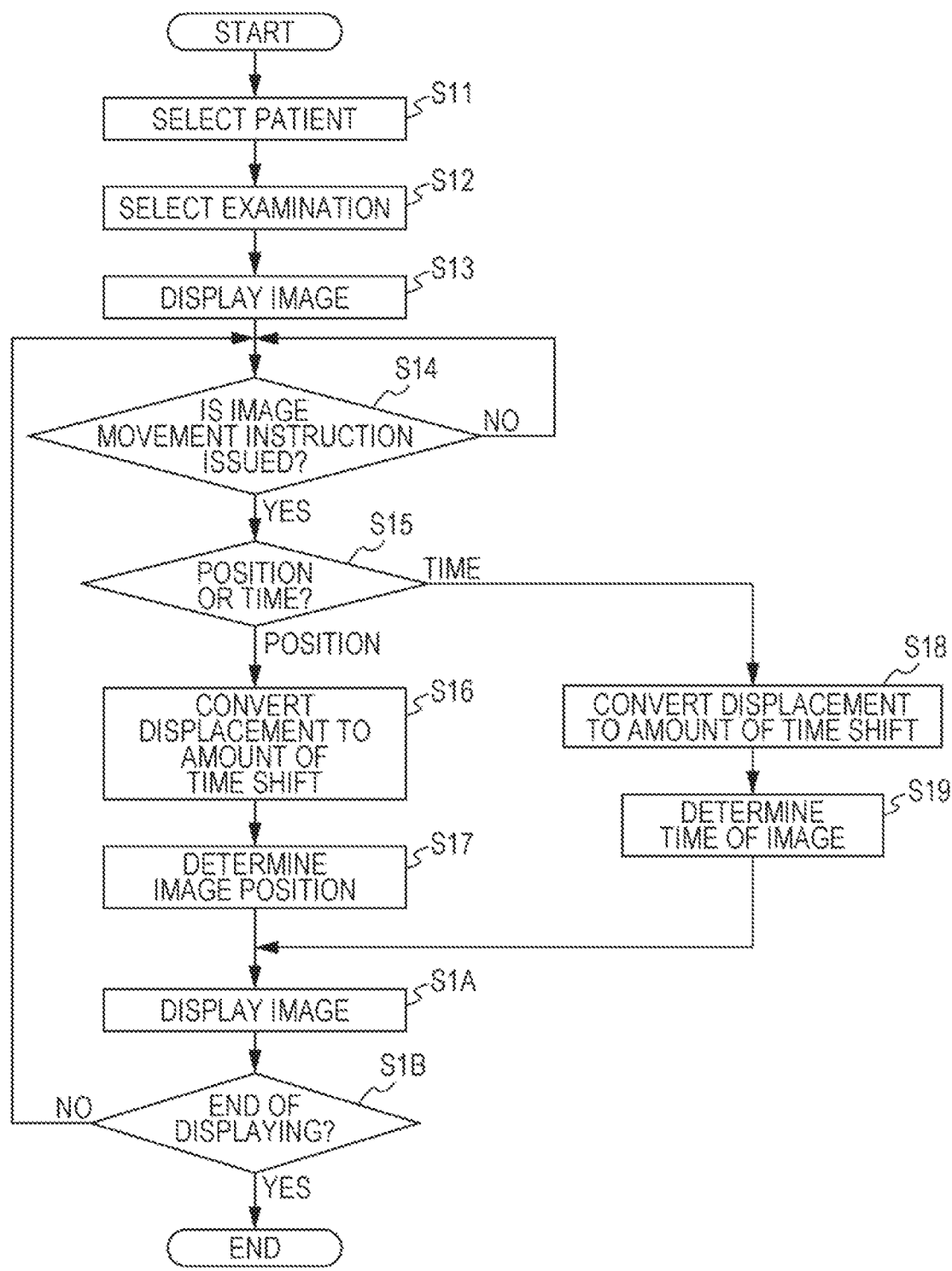
FIG. 4 is a flow chart illustrating a process of displaying tomographic images according to the first embodiment.

Referring to a flow chart shown in FIG. 4, a process of displaying a tomographic image according to the present embodiment is described below.

First, according to an operation input performed on the input device 100 by a user, the user input obtainer 20 selects a patient whose tomographic image is to be displayed (S11). For example, when a patient list such as that shown in FIG. 5 is displayed on the display device 200, the user input obtainer 20 may select a patient ID of a patient specified by the input device 100. Herein, it is assumed by way of example that "0002" is selected.

Next, the user input obtainer 20 selects an examination whose tomographic image is to be displayed for the patient selected in step S11, based on an operation input on the input device 100 by a user (S12). For example, when an examination list such as that shown in FIG. 6 is displayed on the display device 200, the user input obtainer 20 selects an examination specified via the input device 100. Herein, it is assumed by way of example that an examination performed on an examination date of "02.03.2013" is selected.

Thereafter, the tomographic image of the examination selected in step S12 is displayed (S13). Preferably, but not necessarily, the tomographic image displayed here is a typical tomographic image in the tomographic image set captured in the examination.

Figure 7:
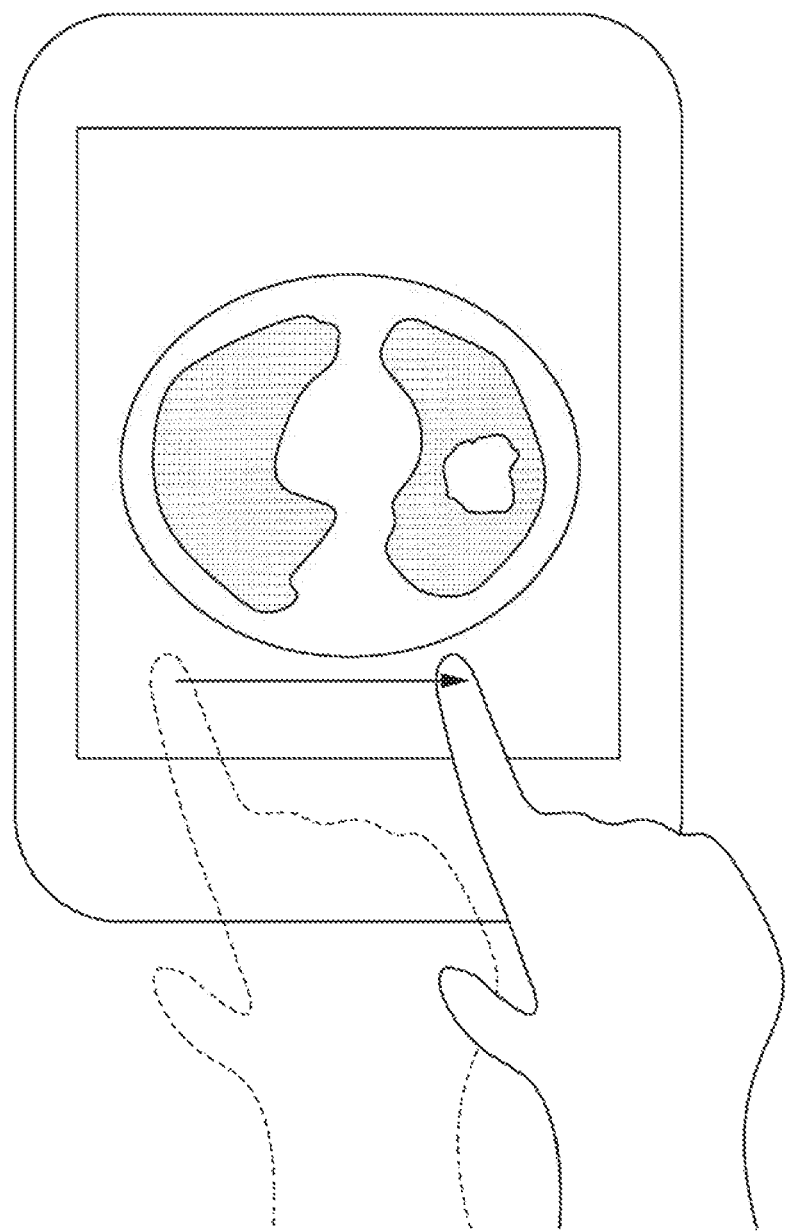
FIG. 7 is a diagram conceptually illustrating a manner of performing an input operation on a tablet.

Thereafter, the user input obtainer 20 waits for an image movement instruction to be input via the input device 100 (S14). If the user input obtainer 20 receives an image movement instruction (YES in S14), then processing flow proceeds to step S15. The image movement instruction received here includes identification information specifying whether a slice position is to be moved (a slice position shift) or an image capture time is to be moved (an image capture time shift), and also includes a displacement amount specified by a user operation. For example, in a case where the input device 100 is a touch panel such as that shown in FIG. 7, for example, the identification information may be information indicating whether a dragging operation was performed in a vertical direction or a horizontal direction, and the distance of the dragging operation may indicate the displacement amount. In step S15, a determination is performed as to whether a position or a time is to be changed in the image movement. When the identification information specifies that the slice position shift is to be performed, the processing flow proceeds to step S16. On the other hand, when the identification information specifies that the image capture time shift is to be performed, the processing flow proceeds to step S18.

In step S16, the slice position selector 25 converts the displacement amount described in the image movement instruction to a moving distance of the slice position. According to this moving distance, a position of a tomographic image to be displayed next is determined (S17). Note that the tomographic image to be displayed next herein is selected from a tomographic image set including the tomographic image being currently displayed, that is, from a set of tomographic images captured at the same time as that of the tomographic image being currently displayed. The slice position selector 25 sends the image ID of the determined tomographic image to the displaying image obtainer 30.

Figure 8:
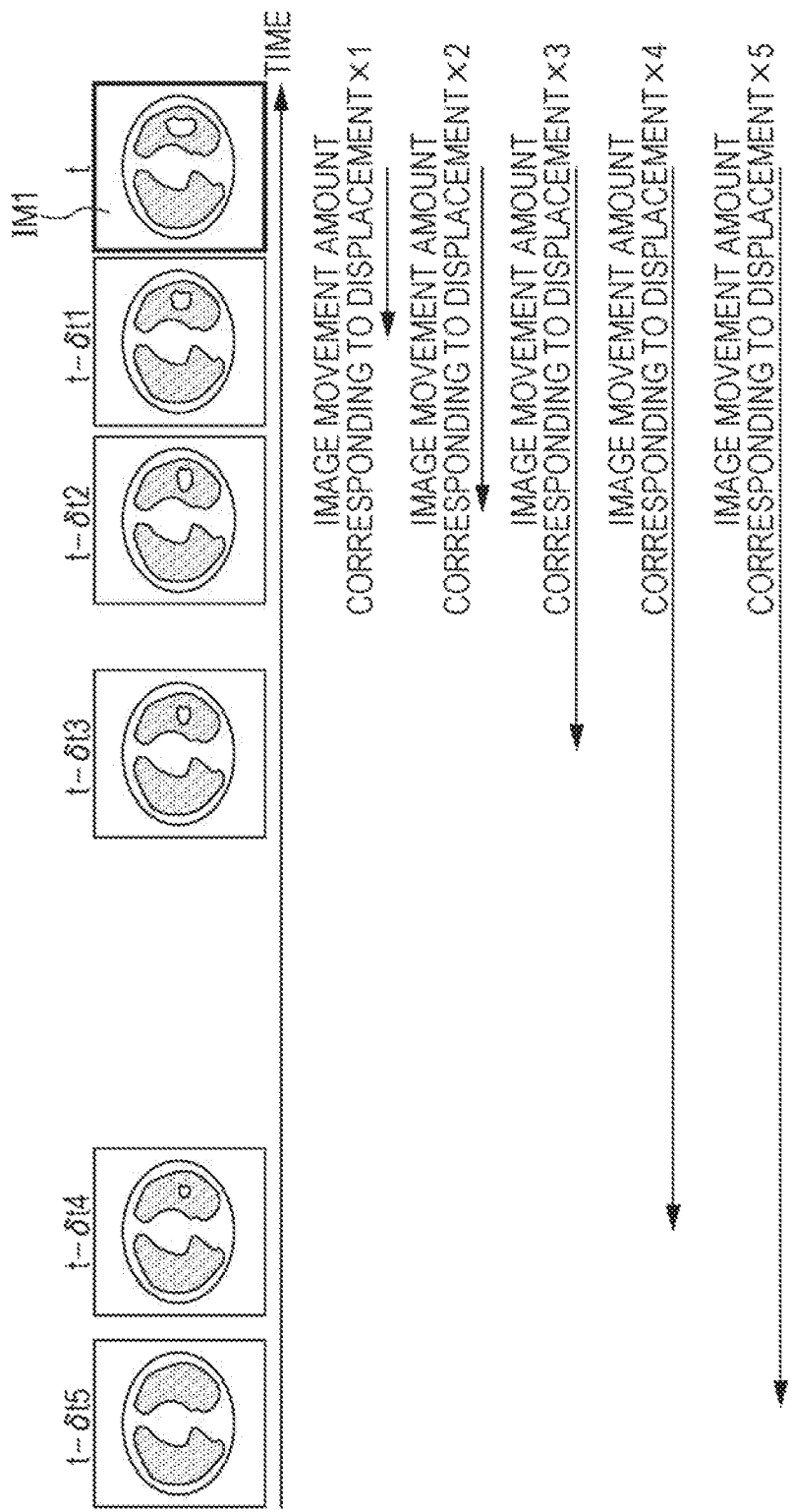
FIG. 8 is a diagram conceptually illustrating an image-capture-time shift on a tomographic image according to the first embodiment.

On the other hand, in step S18, the image capture time selector 26 converts the displacement amount described in the image movement instruction to an amount of shift of the image capture time. According to this amount of shift, the image capture time selector 26 determines an image capture time of the tomographic image to be displayed next (S19). Note that the tomographic image to be displayed next is determined from tomographic image sets that are identical in terms of the patient, the examination portion, and the modality to the tomographic image being currently displayed but that are different in terms of the image capture time. Herein it is assumed by way of example that the number of tomographic images moved in time is proportional to the displacement amount as shown in FIG. 8. The image capture time selector 26 sends the image ID of the determined tomographic image to the displaying image obtainer 30. Note that the image capture time of the tomographic image set may be the earliest image capture time of all image capture times of tomographic images included in the tomographic image sets.

The displaying image obtainer 30 reads out, from the image storage device 300, the tomographic image determined by the slice position selector 25 or the image capture time selector 26, and supplies the resultant tomographic image to the display information generator 35. In this reading process, it is assumed that the tomographic image is read out from the registered image storage unit 320. The display information generator 35 generates display information including the tomographic image received from the displaying image obtainer 30 and displays the result on the display device 200 (S1A).

Each time the user input obtainer 20 receives an image movement instruction, the process in steps S15 to S1A is repeated. When a user inputs a case display end command using the input device 100 (YES in SIB), the process is ended.

Figure 9:
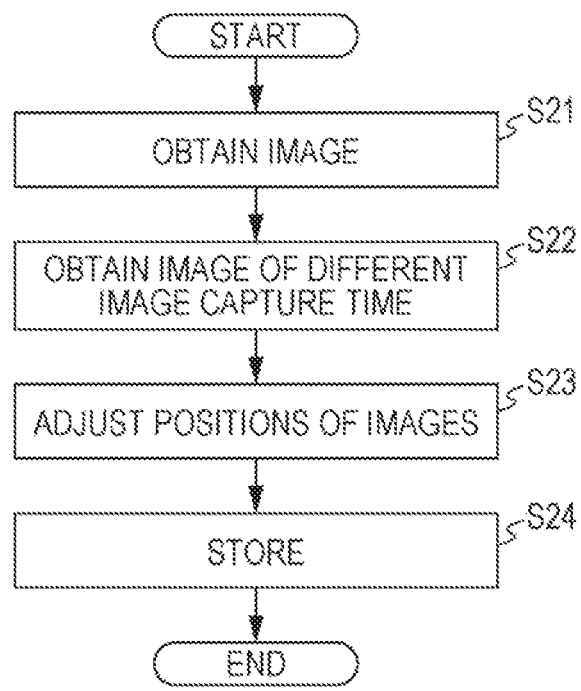
FIG. 9 is a flow chart illustrating a process of adjusting positions of images.

FIG. 9 is a flow chart illustrating a process of adjusting positions of images. First, the captured image obtainer 40 acquires a tomographic image set captured by the medical imaging device 400 (S21). The different-capture-time image obtainer 42 acquires, from the diagnostic image storage unit 310, a tomographic image set identical to the tomographic image set acquired in step S21 in terms of the patient, the examination portion, and the modality but different in terms of the image capture time (322).

The registered image generator 45 performs the organ position registration between the tomographic image set acquired in step S21 (a tomographic image set P) and the tomographic image set acquired in step S22 (a tomographic image set Q) (S23). The image registration may be performed by selecting, from the tomographic image set Q, a tomographic image having the highest correlation with a specific tomographic image included in the tomographic image set P. Herein, as an example, let it be assumed that there are 50 tomographic images included in the tomographic image set P, and they are sequentially identified by numbers from P1 to P50. Similarly, let it be assumed that there are 50 tomographic images included in the tomographic image set Q, and they are sequentially identified by numbers from Q1 to Q50. A tomographic image identified by P25 at a middle of the tomographic images identified by P1 to P50 is selected, and a tomographic image with the highest correlation to the tomographic image identified by P25 is selected from the tomographic images included in the tomographic image set Q. Let it be assumed by way of example that the tomographic image selected here is a tomographic image identified by Q20. In this case, a tomographic image identified by P6 corresponds to a tomographic image identified by Q1, a tomographic image identified by P7 corresponds to a tomographic image identified by Q2, the tomographic image identified by P25 corresponds to a tomographic image identified by Q20, and a tomographic image identified by P50 corresponds to a tomographic image identified by Q45. That is, a tomographic image identified by Pn+5 corresponds to a tomographic image identified by Qn (where n is a positive integer equal to or smaller than 45). Note that the selected specific tomographic image may be a tomographic image including no lesion. After the image registration is completed, the resultant tomographic images are stored in the registered image storage unit 320.

Although in the flow chart shown in FIG. 9, the image registration is performed when tomographic image sets are acquired, the timing of the image registration is not limited to this. Alternatively, for example, the different-capture-time image obtainer 42 may acquire, at an arbitrary timing, from the diagnostic image storage unit 310, a plurality of different tomographic image sets that are identical to each other in terms of the patient, the examination portion, and the modality but that are different from each other in terms of the image capture time, and the registered image generator 45 may perform the organ position registration for these acquired tomographic image sets.

According to the present embodiment, as described above, the case display apparatus is capable of changing the capturing time of the tomographic image being displayed in accordance with the displacement amount input by a user among tomographic images identical to each other in terms of the patient, the examination portion, and the modality. This makes it possible for a user to easily recognize a change in lesion with time, and thus it becomes possible to easily perform comparative reading.

In the present embodiment, in step S1A, tomographic images are read out from the registered image storage unit 320. This makes it possible to display tomographic images in a manner that allows a viewer to easily recognize the tomographic images when the tomographic images are continuously changed in the time axis. However, it does not necessarily need to use registered images. Alternatively, for example, tomographic images may be read out from the diagnostic image storage unit 310. In this case, the image storage device 300 does not need to include the registered image storage unit 320, and it is allowed to remove the different-capture-time image obtainer 42 and the registered image generator 45 from the case display apparatus 10.

First Modification

In the embodiment described above, it is possible to seamlessly view tomographic images of a plurality of capturing times. That is, in viewing tomographic images that are identical to each other in terms of the patient, the examination portion, and the modality, it is possible to continuously change the image capturing time in accordance with the displacement amount input by a user without operating an examination list, and thus it becomes possible to easily make a comparison among diagnostic images in time series.

Figure 10:
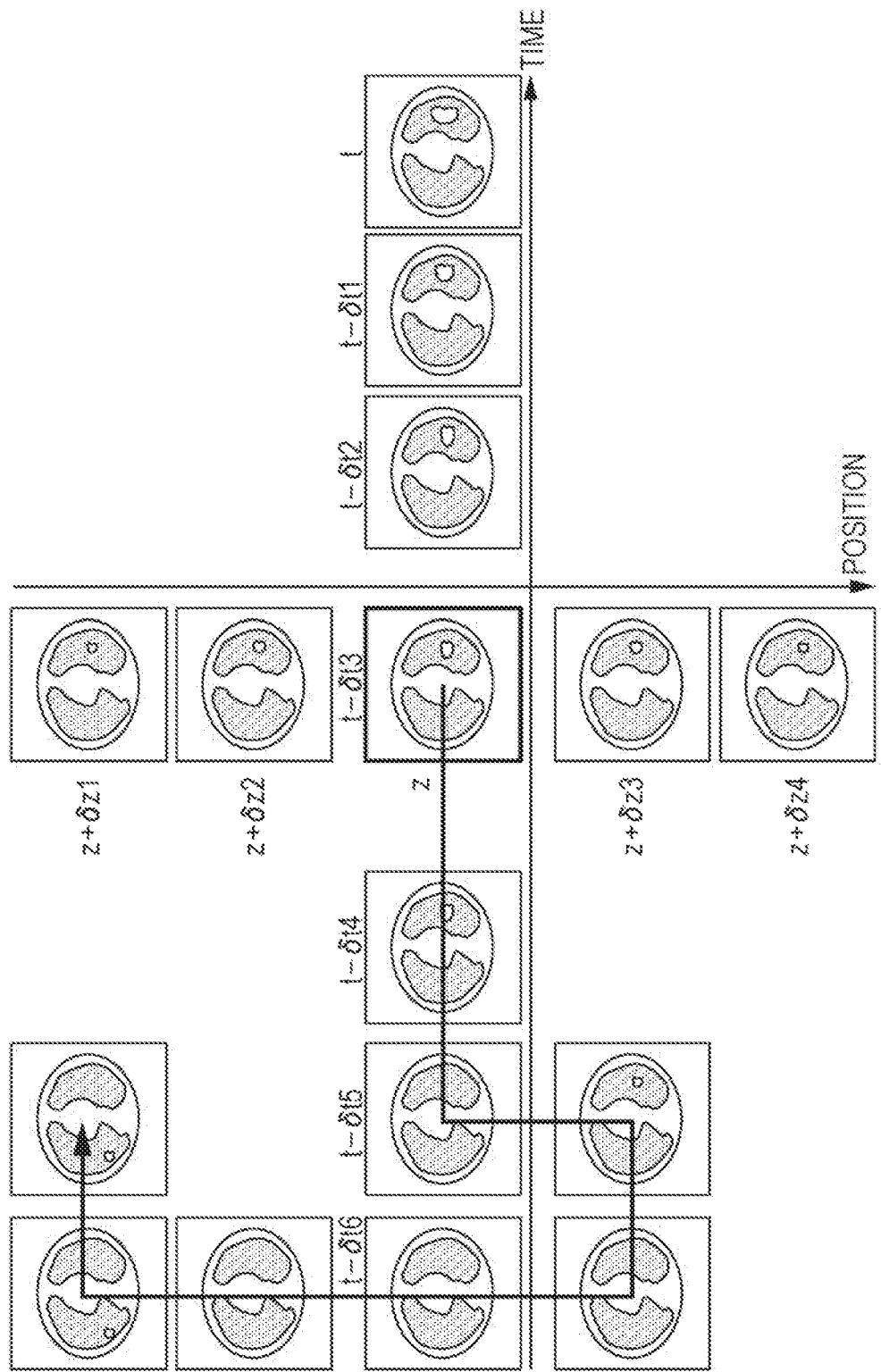
FIG. 10 is a diagram conceptually illustrating a situation in the first embodiment.

However, in a situation in which it is allowed to change the displayed tomographic image in terms of both the slice position and the image capture time as shown in FIG. 10, there is a possibility that it becomes difficult for a user to easily recognize the slice position or the image capture time of the tomographic image being currently displayed. This problem may often occur, for example, when fusion lesions occurs as a result of a change with time, or when a lesion disappears which may occur, for example, in an inflammatory lesion.

Figure 11:
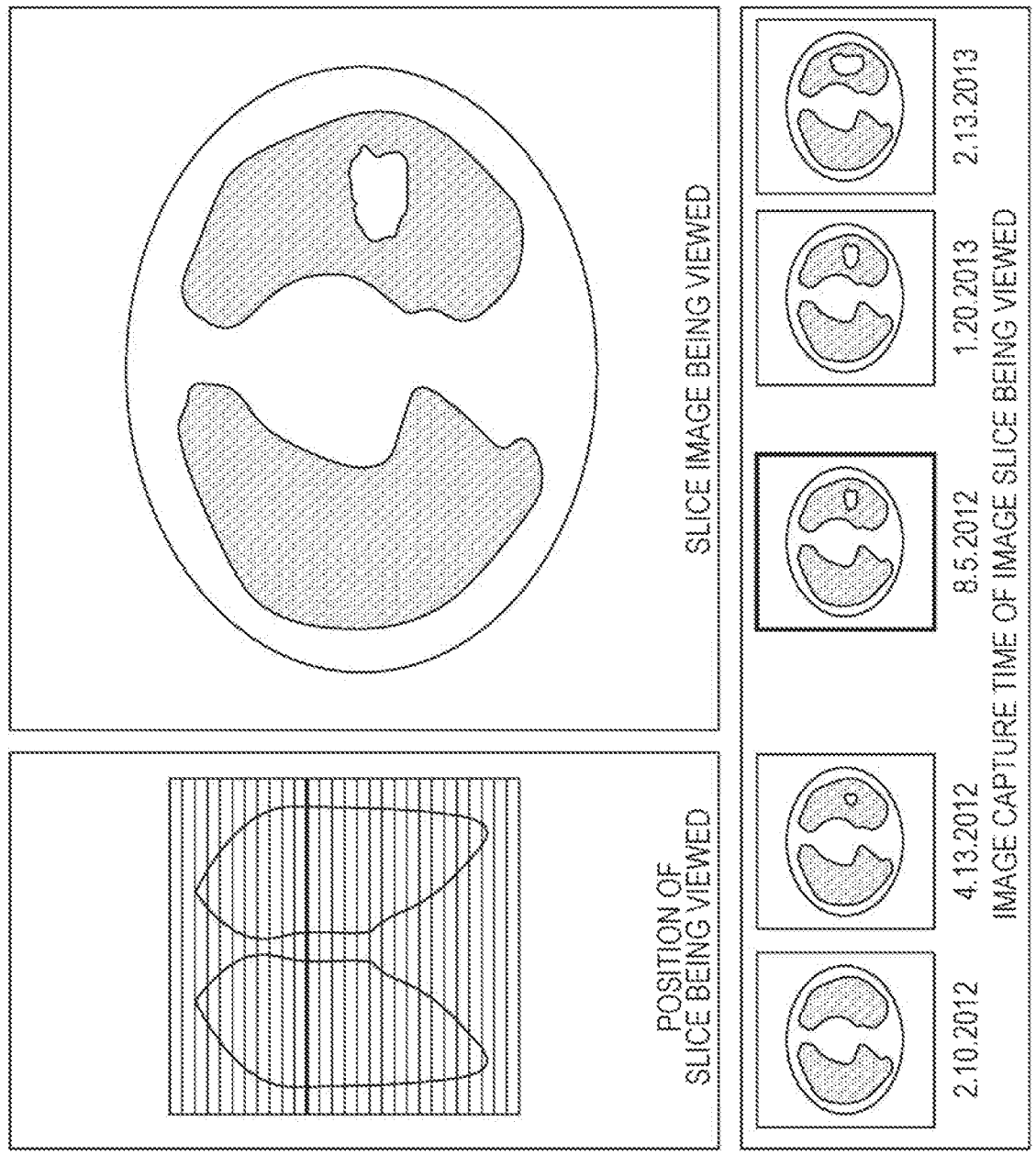
FIG. 11 is a diagram illustrating an example of a modification of a manner in which a screen is displayed according to the first embodiment.

In the present modification, to handle the above situation, when a tomographic image is displayed, information representing the slice position and the image capture time of this tomographic image is also displayed. That is, the display information generator 35 generates the display information to be displayed on the display device 200 such that the display information includes, in addition to a tomographic image received from the displaying image obtainer 30, information representing the slice position and the image capture time of this tomographic image. FIG. 11 illustrates an example of display information according to the present modification. In the example shown in FIG. 11, in addition to a slice image, a slice position and an image capture time corresponding to the slice image being viewed are also displayed. This allows a user to clearly recognize the slice position and the image capture time of the tomographic image being currently displayed.

Second Modification

In the embodiment describe above, when the image capturing time is changed, the tomographic image is changed by skipping as many tomographic images as proportional to the input displacement as illustrated in FIG. 8. That is, the moving distance in the time axis corresponding to the displacement amount is represented by the number of tomographic images. Instead, the displacement amount may be converted to an actual time change, and, based on this time change, the tomographic image at the destination of the image capture time shift may be determined. This process is described in further detail below for a case where an image capture time of a movement destination is calculated assuming that the time change is proportional to the displacement, and a tomographic image to be displayed next is determined based on the calculated image capture time. Note that the manner of converting the displacement amount to the time change is not limited to that based on the proportion.

Figure 12:
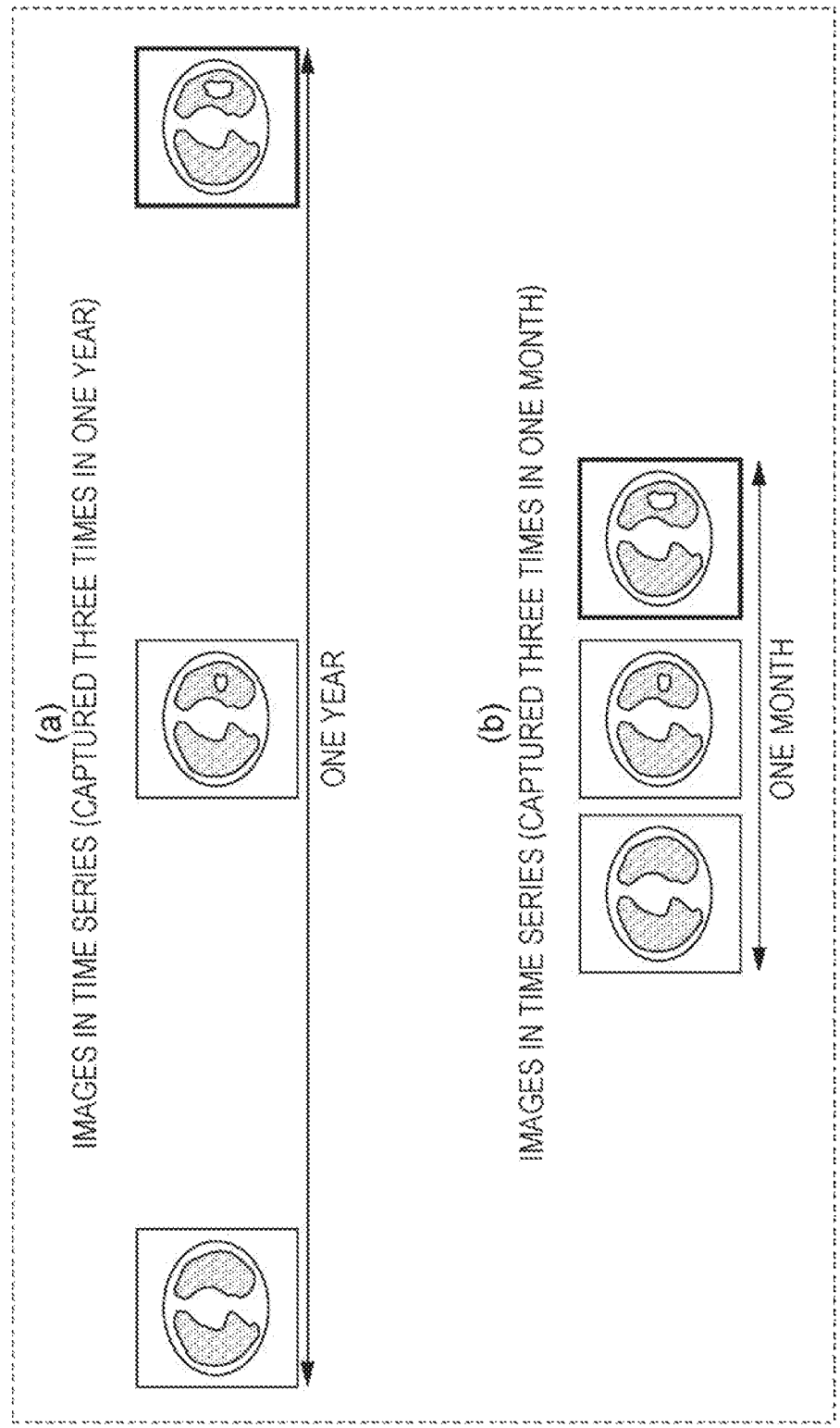
FIG. 12 is a diagram conceptually illustrating a situation in the first embodiment.

As illustrated in FIG. 12, the time interval between adjacent tomographic images varies depending on a patient or a specific examination. In FIG. 12(a), tomographic images are captured three times in one year. FIG. 12(b), tomographic images are captured three times in one month. In these cases, if tomographic images are skipped such that the number of skipped tomographic images is proportional to the displacement amount, the actual value of the image capture time shift varies depending on the time interval of capturing tomographic images. As a result, in the example in FIG. 12, the change occurring in one year in the example in FIG. 12(a) seems to be temporally identical to the change occurring in one month in the example in FIG. 12(b). For example, when one patient is subjected to a small number of examinations in a long period of time and another patient is subjected to a large number of examinations in a short period of time, there is a possibility that an apparent rate of the change in lesion seems to be greater for one of two patients than the other patient although the actual rate may be greater for the other patient. That is, in the embodiment described above, when a user observes a change in a lesion with time, there is a possibility that an apparent value of the image capture time shift performed in response to a moving operation of a mouse may be perceived by a user as if the perceived value is different from the actual value of the image capture time shift. This problem does not occur for slice positions of tomographic images because tomographic images are generally captured at fixed intervals of physical distance. However, when images are moved in terms of the image capture time, the not-fixed time interval of capturing tomographic images can cause the above-described problem to occur.

In view of the above, in the present modification, the image capture time selector 26 determines an image capture time for an image to be obtained as a result of the image capture time shift by calculating it assuming that the change in the image capture time is proportional to the displacement described in the image movement instruction, and selects a tomographic image to be displayed next based on the calculated image capture time. Herein, for example, a tomographic image with an image capture time closest to the calculated image capture time may be selected. Alternatively, the tomographic image to be displayed may be selected such that an image capture time closest to the calculated image capture time may is detected from tomographic images in a range of the image capture times between the image capture time of the tomographic image being currently displayed and the calculated image capture time, and the detected tomographic image may be employed.

As a result, the image capture time is changed in proportional to the displacement regardless of the time interval of capturing images or the number of times the image was captured. Thus, in changing of the image capture time of the tomographic image, it becomes possible for a user to feel that the value of the change in the image capture time well corresponds to the operation amount of the input device.

Third Modification

Figure 13:
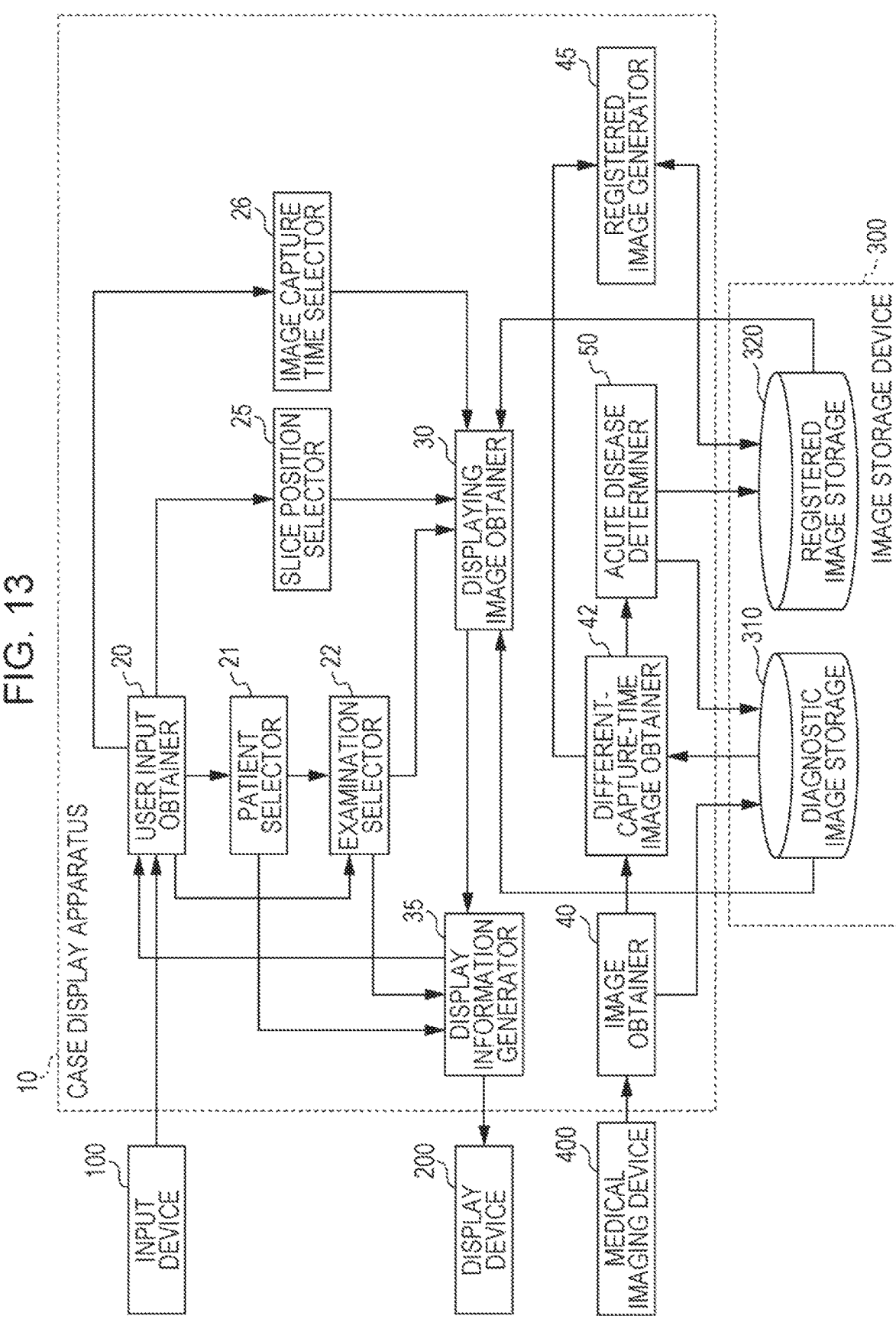
FIG. 13 is a block diagram illustrating a modification of a functional configuration of a case display apparatus according to the first embodiment.

FIG. 13 is a block diagram illustrating a functional configuration of a case display apparatus according to a third modification of the first embodiment. In the configuration shown in FIG. 13, the case display apparatus 10 further includes an acute disease determiner 50 that adds acuteness information to a particular tomographic image. The acuteness information is information indicating that a lesion included in the tomographic image is acute. When the display information generator 35 receives a tomographic image from the displaying image obtainer 30, if the received tomographic image has acuteness information added thereto, then the display information generator 35 generates display information to be displayed on the display device 200 such that an indicator indicating acuteness is added to the tomographic image.

Figure 14:
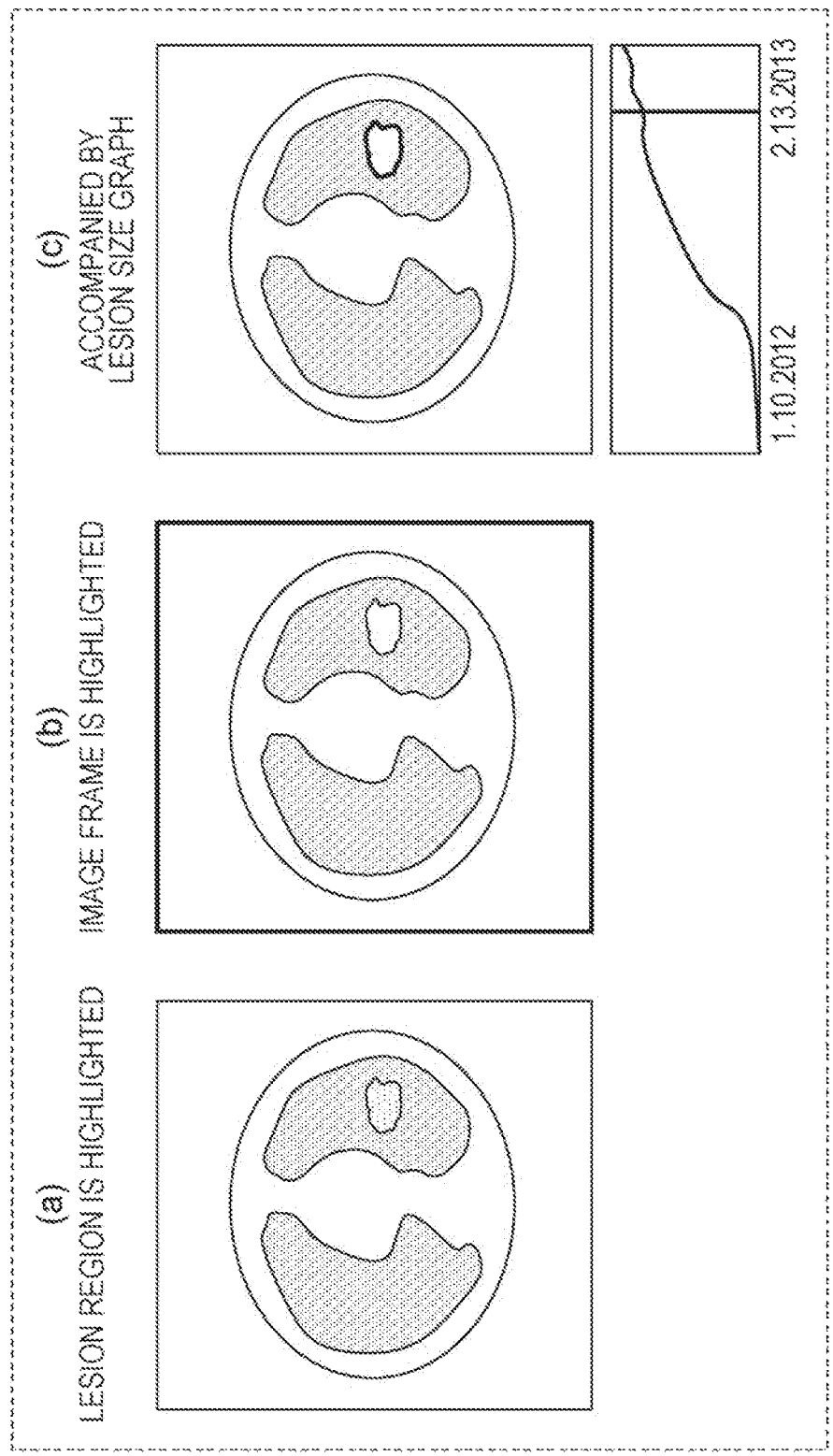
FIG. 14 is a diagram illustrating a manner in which a sick region is acute.

FIG. 14 illustrates a manner in which a sick region is acute. In an example shown in FIG. 14(*a*), a lesion region is highlighted with a color or the like. In an example shown in FIG. 14(*b*), an image frame is highlighted. In an example shown in FIG. 14(*c*), a tomographic image is accompanied by a graph representing a change in lesion size. By adding such an indicator, it becomes possible for a user to easily notice an acute lesion when the user changes the tomographic image in terms of the image capture time, which prevents the user from missing the acute lesion.

A description is given below as to an example of an operation of determining whether a lesion is acute or not and adding acuteness information to a tomographic image if necessary according to the present modification. Note that this operation may be performed, for example, when the captured image obtainer 40 acquires a tomographic image set, or may be performed at another proper timing.

The different-capture-time image obtainer 42 reads out, from the image storage device 300, a plurality of tomographic image sets that are identical to each other in terms of a patient, an examination portion, and a modality, and the different-capture-time image obtainer 42 outputs the acquired tomographic image sets to the acute disease determiner 50. The acute disease determiner 50 extracts a lesion region from each tomographic image set and calculates the volume of each lesion region. To extract the lesion region from each tomographic image, for example, a method disclosed in Yamamoto, et al., "Development of Computer-aided Diagnostic System for Detection of Lung Nodules in Three-dimensional Computed Tomography Images", Japanese Journal of Radiological Technology Vol. 62 (2006) No, 4, pp. 555-564 may be employed. The volume of each lesion region may be calculated from the number of pixels included in the extracted lesion region and the pixel-to-pixel distance. For example, the calculation may be performed using the number of boxels.

The acute disease determiner 50 then calculates a change with time in volume of the lesion region using the calculated volume of the lesion region and the image capture time of each tomographic image set. In a case where the change with time is equal to or greater than a predetermined threshold value, it is determined that the lesion is acute. When it is determined that the lesion is acute, acuteness information is added to a tomographic image including the lesion.

The present modification ensures that a user can notice an acute lesion regardless of the time interval between adjacent examinations or the variation of the operation amount given by a user, which prevents the acute lesion from being missed.

Second Embodiment

Figure 15:
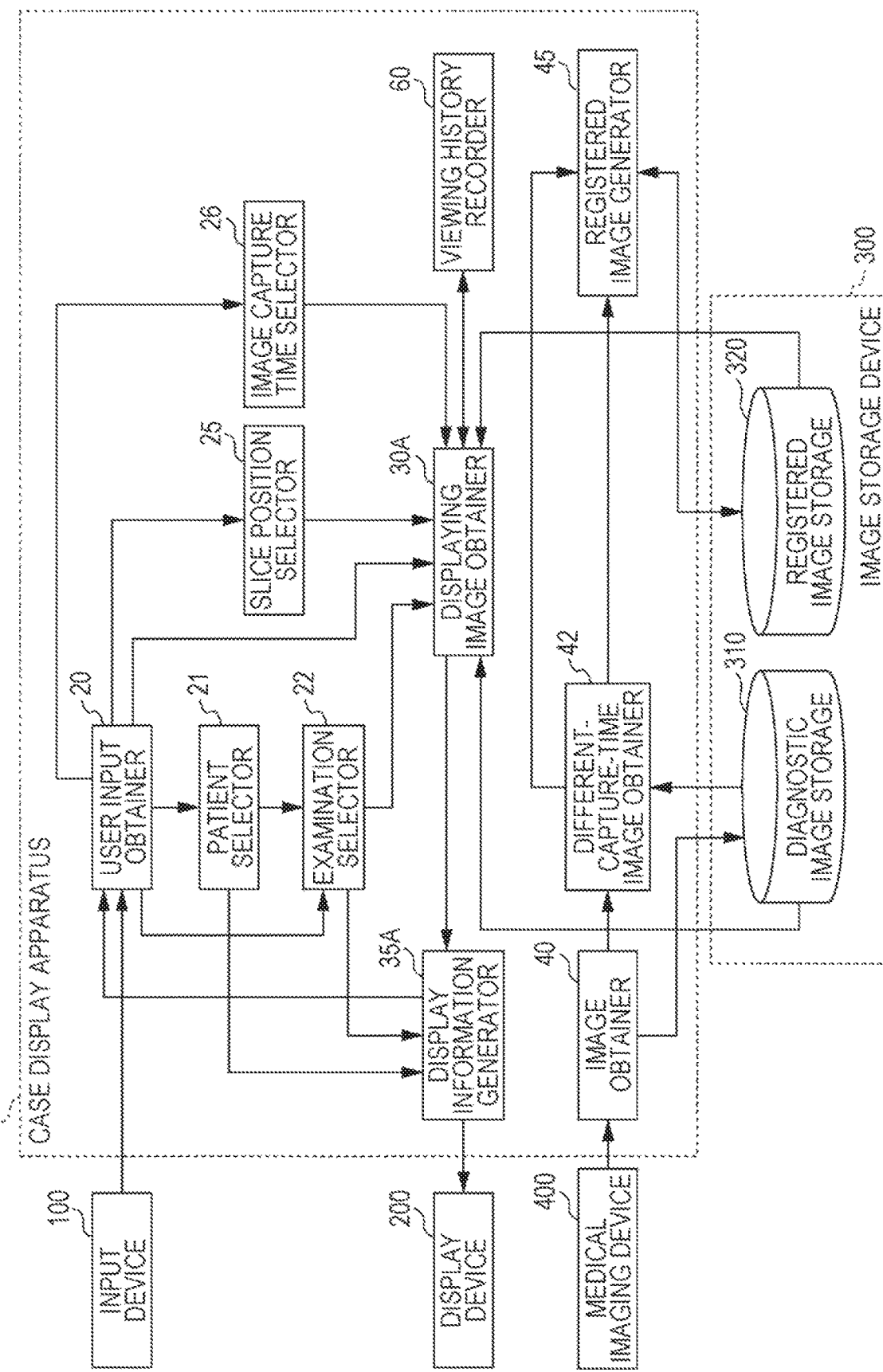
FIG. 15 is a block diagram illustrating a functional configuration of a case display apparatus according to a second embodiment.

FIG. 15 is a block diagram illustrating a functional configuration of a case display apparatus according to a second embodiment. In FIG. 15, constituent elements similar to those in FIG. 1 are denoted by similar reference numerals, and a further detailed description thereof is omitted unless necessary. The case display apparatus 10 in FIG. 15 includes, in addition to constituent elements shown in FIG. 1, a viewing history recorder 60 that records a viewing history including a past image movement instruction.

In the configuration shown in FIG. 15, in a case where the user input obtainer 20 does not receive a new image movement instruction within a predetermined period of time after an image capture time shift is performed on a tomographic image, a displaying image obtainer 30A and a display information generator 35A control displaying such that the slice position of the displayed tomographic image is moved up and down in a tomographic image set including a tomographic image being currently displayed. Regarding the other functions, the displaying image obtainer 30A and the display information generator 35A are respectively similar to the displaying image obtainer 30 and the display information generator 35 according to the first embodiment.

Figure 16:
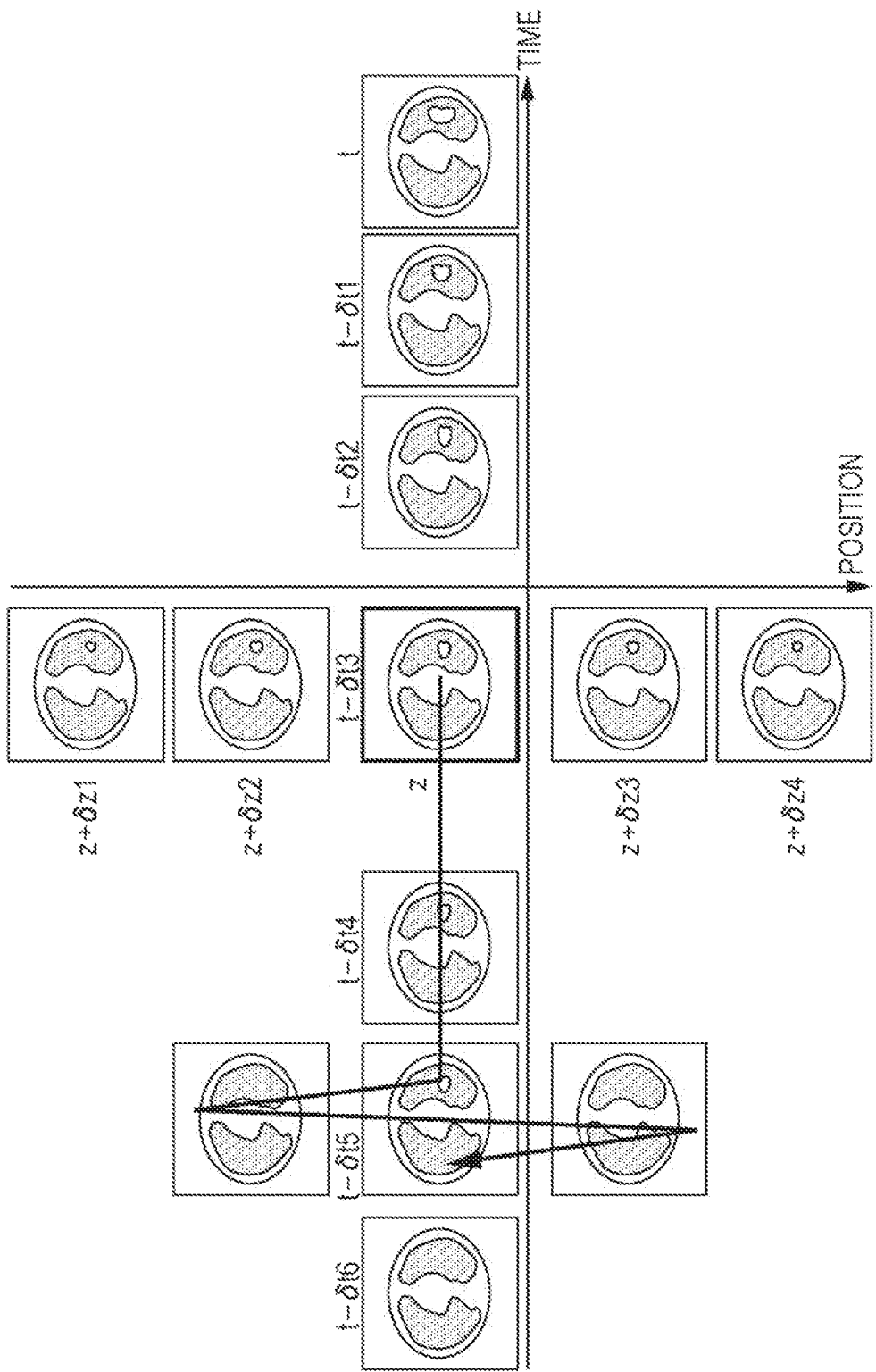
FIG. 16 is a diagram conceptually illustrating a manner in which tomographic images are displayed according to the second embodiment.

FIG. 16 is a diagram conceptually illustrating a manner in which tomographic images are displayed according to the present embodiment. In a case where when an image capture time is shifted such that a tomographic image of a capturing time (t−δt3) being currently displayed is moved to a tomographic image of capturing time (t−δt5) as illustrated in FIG. 16, if no image movement instruction is issued in a predetermined period of time thereafter, the slice position is moved up and down at the imaging time (t−δt5).

When a user, that is, a doctor, changes the image capture time of the tomographic image being displayed, the user is likely to move the slice position up and down to recognize a 3-dimensional shape of a lesion of that image capture time. However, in the first embodiment, to move the slice position up and down each time the user changes the image capture time, it is necessary to frequently switch the movement mode between the time and the position, that is, the user has to perform a troublesome operation. Furthermore, in viewing a change in a lesion with time, the displayed image may be often shifted from the slice position of interest, which may make it difficult to accurately recognize the change with time. The present embodiment handles such a situation.

Figure 17:
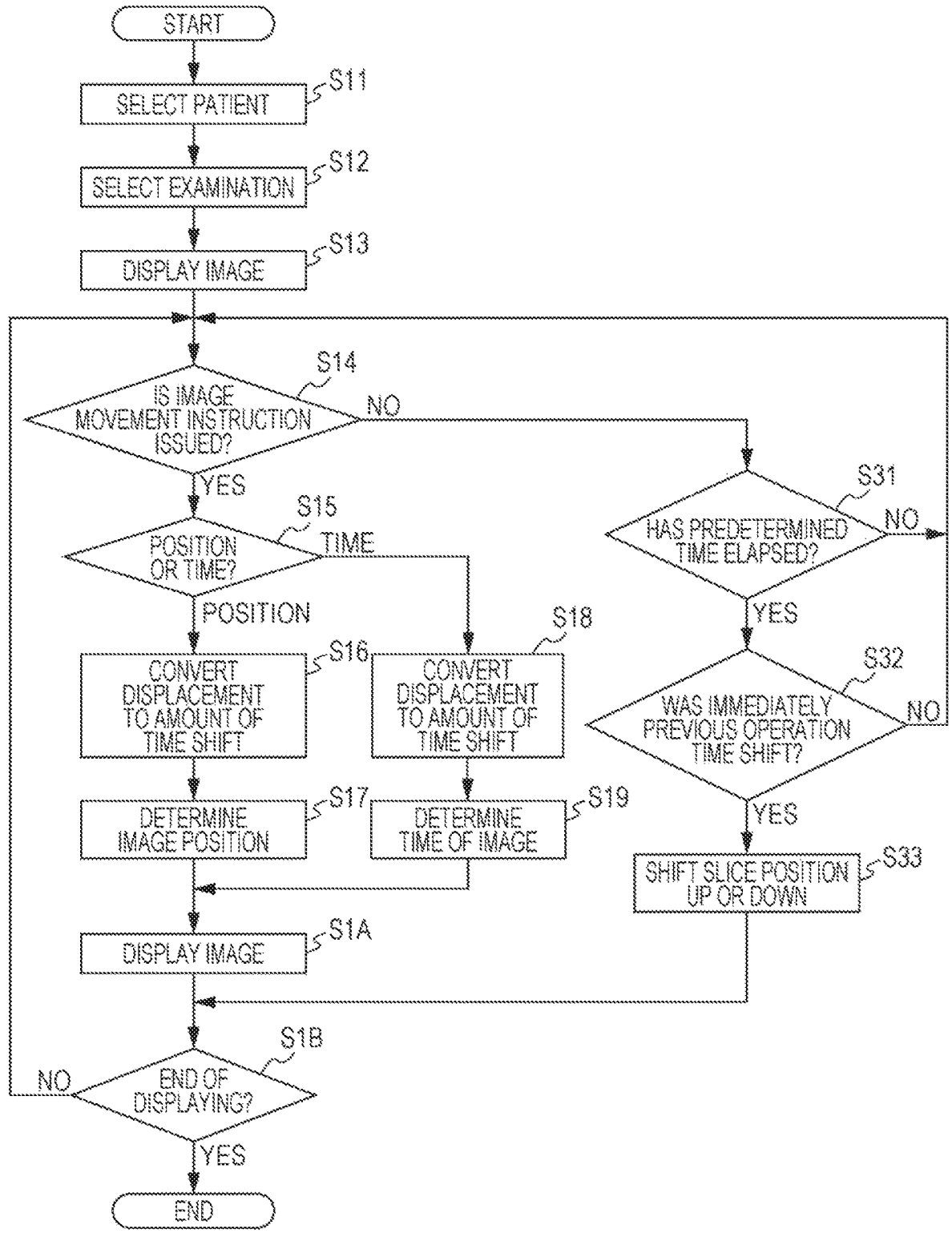
FIG. 17 is a flow chart illustrating a process of displaying tomographic images according to the second embodiment.

Referring to a flow chart shown in FIG. 17, a process of displaying a tomographic image according to the present embodiment is described below. Note that in FIG. 17, steps similar to those in FIG. 4 are denoted by similar reference symbols, and a further description thereof is omitted unless necessary.

The user input obtainer 20 determines whether a predetermined period of time has elapsed without receiving an image movement instruction from the input device 100 (S31). The predetermined period of time may be set, taking into account the usual user operation, for example, to about 3 seconds. If the predetermined period of time has elapsed (YES in S31), it is determined whether the immediately previous operation was an image capture time shift or not (S32). In a case where the immediately previous operation was an image capture time shift (YES in S32), the user input obtainer 20 notices the displaying image obtainer 30A that the predetermined period of time has elapsed since the image capture time shift was performed, and the processing flow proceeds to step S33. In a case where the predetermined period of time has not yet elapsed (NO in S31) or in a case where the immediately previous operation was not an image capture time shift but a slice position shift (NO in S32), the processing flow returns to step S14.

In step S33, the displaying image obtainer 30A and the display information generator 35A control displaying so as to move the slice position up and down. More specifically, the displaying image obtainer 30A reads out, from the image storage device 300, a predetermined number of tomographic images in a range adjacent in terms of slice position to the tomographic image being currently displayed, and the displaying image obtainer 30A outputs the acquired tomographic images to the display information generator 35A. The display information generator 35A displays the predetermined number of tomographic images received from the displaying image obtainer 30A on the display device 200 while moving the position up and down.

The range of read-out tomographic images is determined referring to a past history in terms of slice position shift recorded in the viewing history recorder 60. That is, the amount of up-and-down movement of the slice position is determined from the history of the slice position shift described in the viewing history. For example, the average value of the number of images moved in terms of the slice position immediately after the image capture time shift is calculated, and the number of tomographic images to be read out may be set to be equal to this average value.

According to the present embodiment, as described above, the tomographic image is automatically moved in the direction in which the slice position varies after the imaging time of the tomographic image is changed.

In the present embodiment, it is assumed by way of example that the amount of up-and-down movement of the slice position after the image capture time shift is determined based on the past viewing history, the manner of determining the amount of up-and-down movement is not limited to this. For example, the number of images to be moved up and down may be fixed in a particular range, for example, to 5 images or the like including the current tomographic image. Alternatively, the determination may be made based on the size of the lesion in the tomographic image sets of interest, or, in a case where the lesion is emphysema or the like, the determination may be made based on the extending range of the lesion. More specifically, for example, the determination may be made based on the volume of the lesion region calculated using the method described above according to the third modification of the first embodiment, or based on the number of tomographic images including the lesion in the tomographic image sets of interest.

Figure 21:
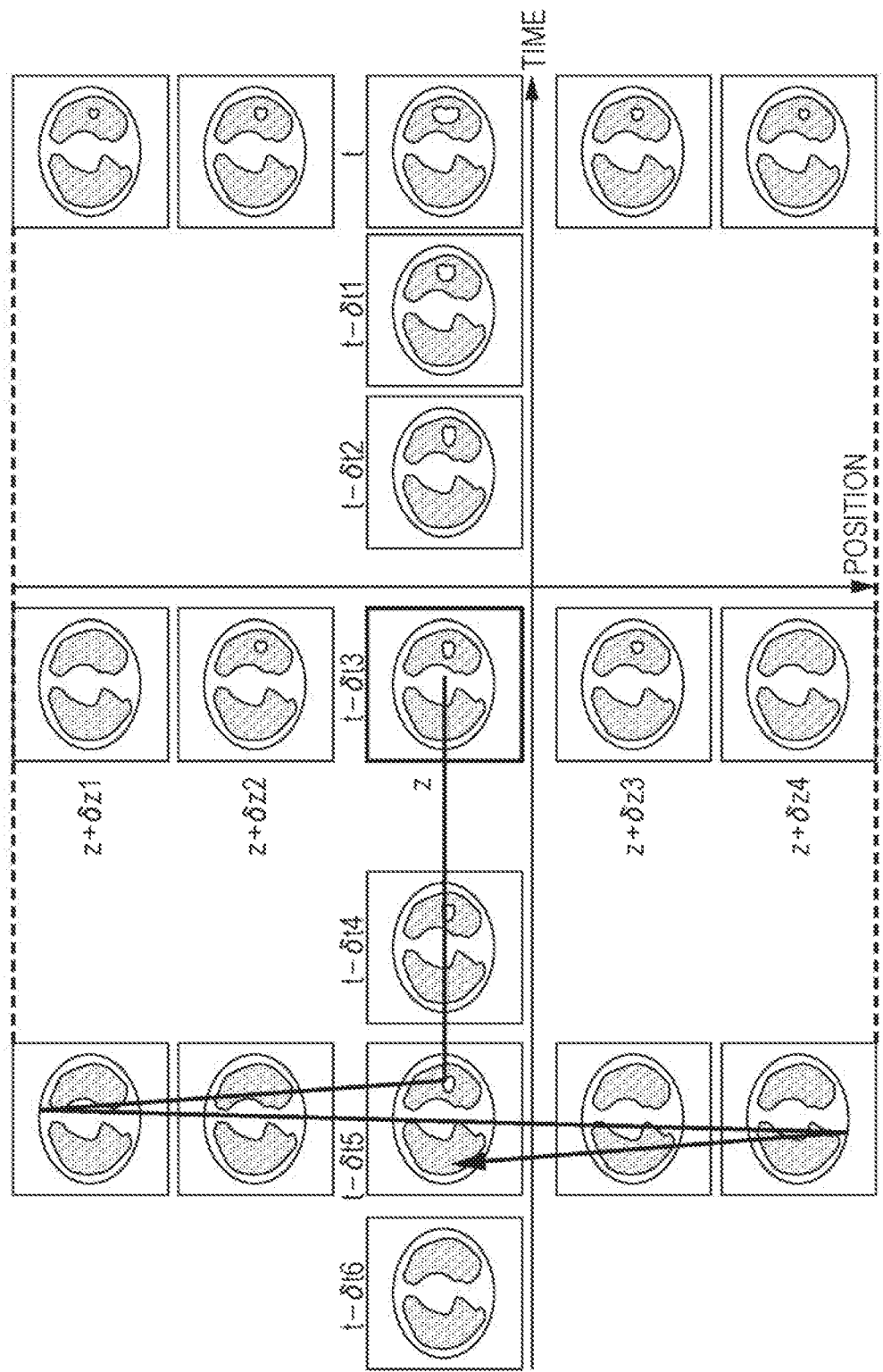
FIG. 21 is a diagram conceptually illustrating a manner in which tomographic images are displayed according to the second embodiment.

The amount of the up-and-down movement of the slice position after the image capture time shift may be determined not only based on the information associated with the tomographic image sets of interest but also based on information associated with a plurality of tomographic image sets that are identical to the present tomographic image set in terms of the patient, the examination portion, and the modality but that are different from each other in terms of the image capture time. For example, as illustrated in FIG. 21, for a tomographic image set (an imaging time t−δt5) subjected to the displaying process, the amount of up-and-down movement of the slice position may be determined based on sizes or ranges of lesions in tomographic image sets of different imaging times (image times t−δt6 to imaging time t) of a patient of interest. In the example illustrated in FIG. 21, in a tomographic image set of an imaging time (time t) at which the lesion has a maximum size, the amount of the up-and-down movement of the slice position is determined depending on the number of tomographic images including a lesion. Alternatively, for example, the determination may be made based on the volume of the lesion region calculated using the method described above according to the third modification of the first embodiment.

By determining the amount of up-and-down movement of the slice position based on the lesion size or range in tomographic image sets of a plurality of imaging times in the manner described above, it becomes possible to display tomographic images such that the tomographic images are moved up and down in a range that is necessary and sufficient to perform diagnosis even in a tomographic image set of an image capture time at which a lesion is small or there is no lesion. Displaying tomographic images in such a manner makes it possible to easily recognize which part of normal tissue has changed to a lesion. Thus, it becomes possible for a doctor or the like to accurately recognize a rate of change in lesion, a possibility of spread, a symptom, or the like.

Third Embodiment

Figure 18:
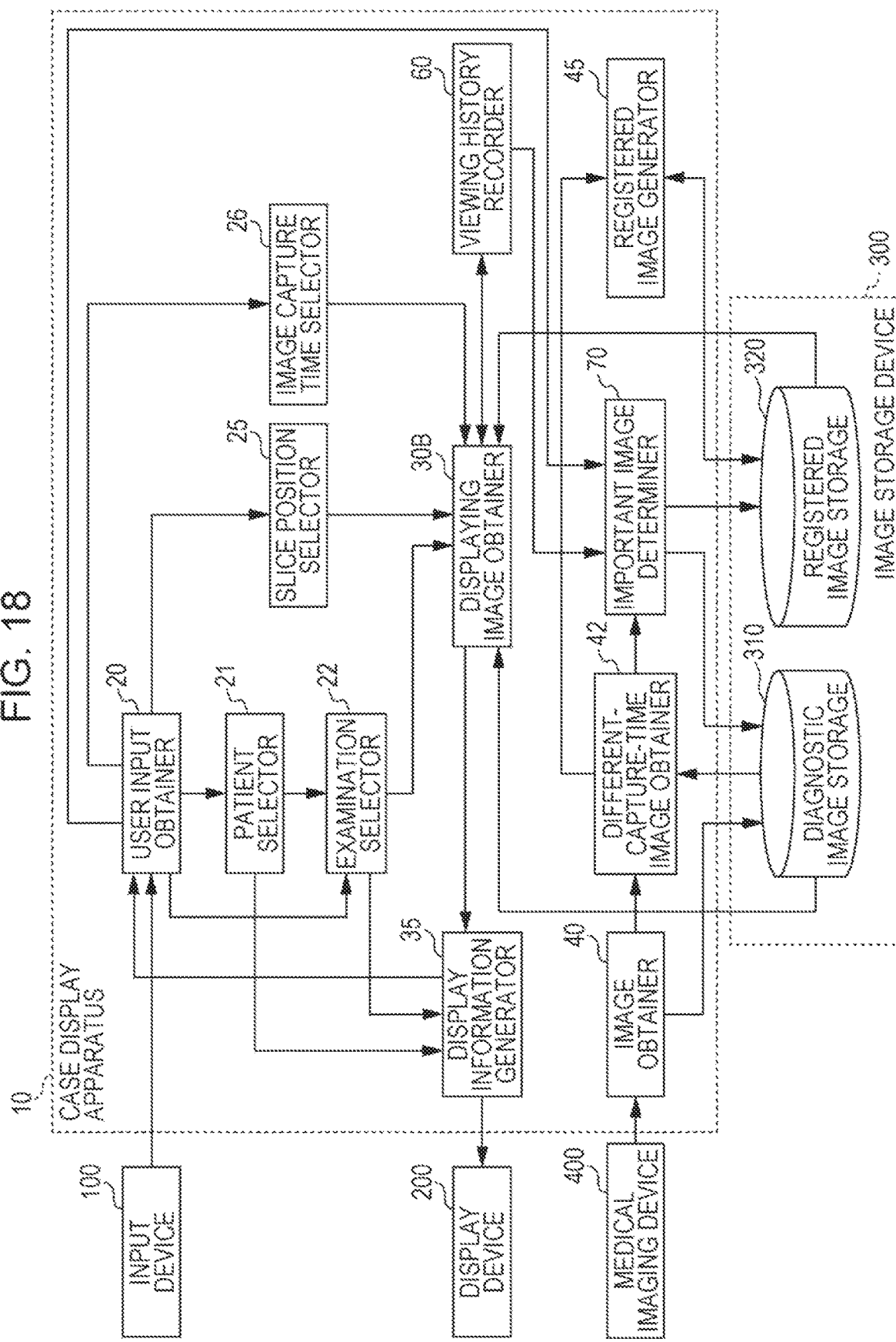
FIG. 18 is a block diagram illustrating a functional configuration of a case display apparatus according to a third embodiment.

FIG. 18 is a block diagram illustrating a functional configuration of a case display apparatus according to a third embodiment. In FIG. 18, constituent elements similar to those in FIG. 1 or FIG. 15 are denoted by similar reference numerals, and a further detailed description thereof is omitted unless necessary. The case display apparatus 10 in FIG. 18 includes, in addition to constituent elements shown in FIG. 15, an importance image determiner 70 that determines an important image among tomographic images stored in the image storage device 300.

In the configuration shown in FIG. 18, part of tomographic images stored in the image storage device 300 are added with importance information indicating that the tomographic image is determined by the importance image determiner 70 as an important image. When the user input obtainer 20 receives an image movement instruction in terms of the image capture time, the displaying image obtainer 30B determines whether there is an important image between the tomographic image and a tomographic image determined by the image capture time selector 26. If there is such an important image, this important image is read out from the image storage device 300 instead of the tomographic image determined by the image capture time selector 26. This important image is displayed by the display information generator 35 on the display device 200. As to other functions, the displaying image obtainer 30B are similar to the displaying image obtainer 30 according to the first embodiment.

Figure 19:
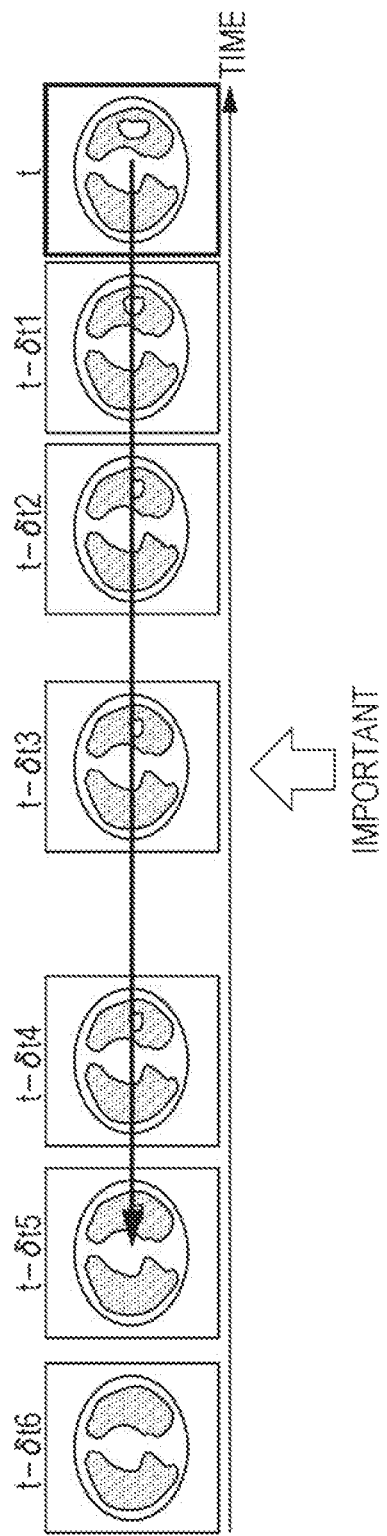
FIG. 19 is a diagram conceptually illustrating a manner in which tomographic images are displayed according to the third embodiment.

The FIG. 19 is a diagram conceptually illustrating a manner in which tomographic images are displayed according to the present embodiment. As illustrated in FIG. 19, in a situation in which a tomographic image captured at time t is currently displayed, when an image movement instruction is issued to move the tomographic image to a tomographic image captured at time (t−δt5), let it be assumed herein that a tomographic image captured at time (t−δt3) is an important image. In this case, the tomographic image is not moved to that captured at time (t−δt5), but to the important image captured at time (t−δt3).

In the image capture time shift of a tomographic image, for example, when the operation amount by a user is large, there is a possibility that an important image located between the current image and the destination image is skipped without being displayed. In the present embodiment, to handle the above situation, in a case where there is an important image between a current tomographic image and a tomographic image specified as a destination of the movement, the movement is stopped at the important image and the important image is displayed. This makes it possible to prevent a user from missing the important image. Furthermore, it becomes easier to search for an important diagnostic image from a large number of diagnostic images.

Figure 20:
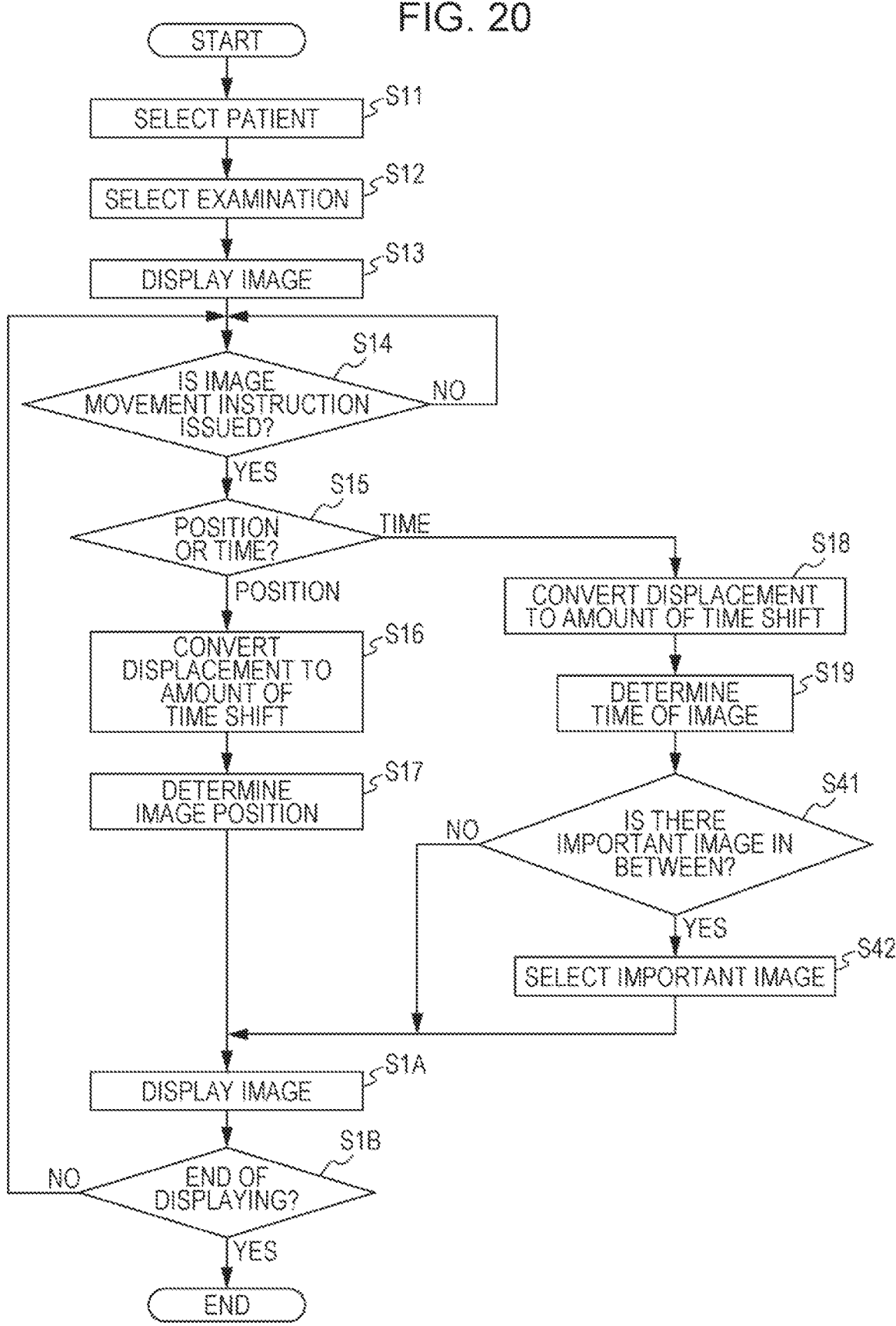
FIG. 20 is a flow chart illustrating a process of displaying tomographic images according to the third embodiment.

Referring to a flow chart shown in FIG. 20, a process of displaying tomographic images according to the present embodiment is described below. Note that in FIG. 20, steps similar to those in FIG. 4 are denoted by similar reference symbols, and a further description thereof is omitted unless necessary.

When the displaying image obtainer 30B receives, from the image capture time selector 26, an image ID identifying a tomographic image specified as a destination of the image capture time shift (S19), the displaying image obtainer 30B determines whether or not there is a tomographic image having importance information attached thereto between a tomographic image being currently displayed and a tomographic image specified as the destination of the movement (S41). In this determination, tomographic images are searched for from tomographic image sets that are stored in the image storage device 300 and that are identical to the tomographic image being currently displayed in terms of a patient, an examination portion, and a modality. When a tomographic image having importance information attached thereto is found (YES in S41), this important image is selected and is read out from the image storage device 300 (S42). On the other hand, in a case where no tomographic image having importance information attached thereto is found (NO in S41), the tomographic image identified by the image ID received from the image capture time selector 26 is read out from the image storage device 300.

In the image capture time shift using the above-described process, when there is an important image between a current tomographic image and a tomographic image specified as a destination of the movement, the movement may be stopped at the important image and the important image may be displayed on the display device 200.

There may be many methods usable as the method of determining an important image by the important image determiner 70. For example, an image feature of a high virulence disease state such as spicula or the like may be extracted in advance as a template in diagnosis, and a diagnostic image may be compared with the template to determine whether the diagnostic image is an important diagnostic image or not. Alternatively, the determination as to the importance may be made depending on the degree of the change with time in the lesion region. In this case, for example, the different-capture-time image obtainer 42 reads out, from the image storage device 300, a plurality of different tomographic image sets that are identical to each other in terms of the patient, the examination portion, and the modality but that are different from each other in terms of the image capture time. Thereafter, the important image determiner 70 detects a change with time in a lesion region by performing image processing on the plurality of tomographic image sets read out. If the rate of the change with time is greater than a predetermined threshold value, the important image determiner 70 determines that a tomographic image including the lesion region in the plurality of tomographic image sets is an important image. Note that this operation may be performed, for example, when the captured image obtainer 40 acquires a tomographic image set, or may be performed at another proper timing.

Alternatively, the determination as to an importance image may be performed referring to a viewing history in terms of tomographic images recorded in the viewing history recorder 60. For example, the important image determiner 70 refers to the viewing history recorder 60 to detect a tomographic image that has been viewed a greater number of times than a predetermined particular number. If such a tomographic image is detected, it is determined as an importance image.

Alternatively, the determination of an importance image may be made manually. For example, in response to receiving an operation input by a user, the important image determiner 70 may add importance information to a tomographic image.

The case display apparatus according to the present disclosure has been described above with reference to specific embodiments. However, the present disclosure is not limited to these embodiments. It will be apparent to those skilled in the art may that many various modifications may be applicable to the embodiments without departing from the spirit and scope of the present disclosure. Furthermore, constituent elements of different embodiments may be combined. In this case, any resultant combination also falls within the scope of the present disclosure.

In a specific example, the case display apparatus may be realized in the form of a computer system including a microprocessor, a ROM, a RAM, a hard disk drive, a display unit, a keyboard, a mouse, and the like. In the RAM or the hard disk drive, a computer program is stored. The microprocessor operates according to the computer program such that the functions of the case display apparatus are achieved. The computer program includes a combination of a plurality of instruction codes which are instructions given to the computer to achieve necessary functions.

Part or all of constituent elements of the case display apparatus may be realized with one system LSI (Large Scale Integration). The system LSI is a super multifunctional LSI produced by integrating a plurality of constituent elements on a single chip. A specific example is a computer system configured using a microprocessor, a ROM, a RAM, and the like. A computer program is stored in the RAM. The microprocessor operates according to the computer program such that the system LSI achieves its functionalities.

Part or all of the constituent elements of the case display apparatus described above may be implemented in the form of an IC card attachable to the case display apparatus or in the form of a single module. The IC card or the module may be a computer system configured using a microprocessor, a ROM, a RAM, and the like. The IC card or the module may include the super multifunctional LSI described above. The microprocessor operates according to the computer program such that the IC card or the module achieves its functionalities. The IC card or the module may be configured so as to be resistant against tampering.

The present disclosure may be implemented as a method. The method may be realized by a computer program that is to be executed by a computer or the method may be realized by a digital signal associated with the computer program.

The present disclosure may be implemented by a computer readable non-temporary storage medium, such as a flexible disk, a hard disk, a CD-ROM disk, a MO disk, a DVD disk, a DVD-ROM disk, a DVD-RAM disk, a BD (Blu-ray (registered trademark) Disc), a semiconductor memory, or the like in which the computer program or the digital signal are stored. The present disclosure may be implemented by the digital signal stored in the non-temporary storage medium.

The present disclosure may be implemented by transmitting the computer program or the digital signal described above via an electric communication line, a wireless or wired communication line, a network typified by the Internet, data broadcasting, or the like.

The present disclosure may be implemented in the form of a computer system including a microprocessor and a memory, wherein the computer program described above is stored and the microprocessor operates according to the computer program.

The present disclosure may be implemented by another separate computer system by storing the computer program or the digital signal described above in the non-temporary storage medium and sending the non-temporary storage medium to the separate computer system or by transmitting the computer program or the digital signal described above to the separate computer system via the network or the like.

The present disclosure allows a user to seamlessly view diagnostic images associated with current diagnosis and past diagnostic images, which makes it easier to perform a comparative reading in terms of a change in disease state. Thus the present disclosure is useful to improve efficiency in the image reading operation performed by a user, i.e., a doctor or the like. The present disclosure is also useful, for example, in training of doctors in terms of image reading techniques or the like.

What is claimed is:

1. A case display apparatus, comprising:
at least one memory configured to store a program; and
at least one processor configured to execute the program and control the case display apparatus to:
generate display information displayed on a display device, including display information associated with a first tomographic image set and a second tomographic image set;
perform position registration by determining images in the second tomographic image set having a highest correlation to images in the first tomographic image set;
when the display information includes a first tomographic image, receive an image movement instruction including identification information and a displacement amount, the identification information indicating a slice position shift or an image capture time shift, wherein there is no medical image except the first tomographic image being displayed on the display when a user gives the image movement instruction;
when the identification information specifies that the slice position shift is to be performed, determine a second tomographic image at a destination of the slice position shift from the first tomographic image set including the first tomographic image, based on a position movement amount corresponding to the displacement amount, the first tomographic image set being a first plurality of tomographic images;
when the identification information specifies that the image capture time shift is to be performed, select, by an image capture time selector, a third tomographic image from the second tomographic image set, the second tomographic image set being a second plurality of tomographic images, a target person of the first tomographic image and target persons of the second tomographic image set being identical, examination portions captured in the first tomographic image set and examination portions captured in the second tomographic image set being identical, a modality for the first tomographic image and modalities for the second tomographic image set being identical, and image capture times of the first tomographic image set and image capture times of the second tomographic image set being different, the third tomographic image selected from the second tomographic image set having a highest correlation with the first tomographic image from the first tomographic image set, an image capture time of the third tomographic image being shifted from an image capture time of the first tomographic image based on a time movement amount corresponding to the displacement amount, wherein the difference between the image capture time of the third tomographic image and the image capture time of the first tomographic image is proportional to the displacement amount; and
read out the second tomographic image or the third tomographic image from an image storage device, and that gives a read out tomographic image to the display information generator;
add importance information to a part of tomographic images stored in the image storage device,
and when the identification information specifies that the image capture time shift is to be performed and there is a fourth tomographic image added with the importance information indicating that the fourth tomographic image is an important image between the first tomographic image and the third tomographic image, read out the fourth tomographic image with the importance information from the image storage device for display instead of the third tomographic image selected by the image capture time selector.

2. The case display apparatus according to claim 1, wherein the at least one processor is further configured to:
read out, from the image storage device, a plurality of tomographic images from the first tomographic image set and the second tomographic image set that are identical in terms of the target person, the examination portion, and the modality but that are different in terms of the image capture time; and
detect a rate of change with time in a lesion region by performing image processing for each of the plurality of tomographic images from the first tomographic image set and the second tomographic image set, and make a determination such that if the rate of change with time is greater than a predetermined threshold value, determine a tomographic image including the lesion region as an important image.

3. The case display apparatus according to claim 1, wherein the at least one processor is further configured to:
record a viewing history of each tomographic image stored in the image storage device; and
determine an important image according to the viewing history.

4. The case display apparatus according to claim 1, wherein the at least one processor is further configured to add importance information to a tomographic image stored in the image storage device in accordance with an operation input by a user.

5. A method of displaying case data with a computer, comprising:
generating display information displayed on a display device, including display information associated with a first tomographic image set and a second tomographic image set;
perform position registration by determining images in the second tomographic image set having a highest correlation to images in the first tomographic image set;
when the display information includes a first tomographic image, receiving an image movement instruction including identification information and a displacement amount, the identification information specifying a slice position shift or an image capture time shift to be performed, wherein there is no medical image except the first tomographic image being displayed on the display when a user gives the image movement instruction;
when the identification information specifies that the slice position shift is to be performed, determining, based on the amount of the position shift corresponding to the displacement amount, a second tomographic image at a destination of the slice position shift from a first tomographic image set that is a first plurality of tomographic images including the first tomographic image;
when the identification information specifies that the image capture time shift is to be performed, determining, by an image capture time selector, a third tomographic image from the second tomographic image set that is a second plurality of tomographic images that are identical to the first tomographic image in terms of a target person, examination portions, and a modality but that are different from the first tomographic image set in terms of an image capture time, the third tomographic image selected from the second tomographic image set having a highest correlation with the first tomographic image from the first tomographic image set, the image capture time of the third tomographic image being shifted from an image capture time of the first tomographic image based on an amount of the image capture time shift corresponding to the displacement amount, wherein the difference between the image capture time of the third tomographic image and the image capture time of the first tomographic image is proportional to the displacement amount;
reading out the second tomographic image or the third tomographic image from an image storage device and newly generating display information including a read-out tomographic image; and
determining one or more tomographic images stored in the image storage device are important images;
wherein importance information is added to the one or more tomographic images stored in the image storage device to indicate that the one or more tomographic images are the important images,
and wherein when the identification information specifies that the image capture time shift is to be performed and there is a fourth tomographic image added with the importance information indicating that the fourth tomographic image is an important image between the first tomographic image and the third tomographic image, the fourth tomographic image with the importance information is read out from the image storage device for display instead of the third tomographic image determined by the image capture time selector.

6. A storage medium including a control program stored therein to control a device including a processor to execute a case displaying process including displaying case data,
the storage medium being a computer-readable non-transitory storage medium, the case displaying process comprising:
generating display information displayed on a display device, including display information associated with a first tomographic image set and a second tomographic image set;
perform position registration by determining images in the second tomographic image set having a highest correlation to images in the first tomographic image set;
when the display information includes a first tomographic image, receiving an image movement instruction including identification information and a displacement amount, the identification information specifying a slice position shift or an image capture time shift to be performed, wherein there is no medical image except the first tomographic image being displayed on the display when a user gives the image movement instruction;
when the identification information specifies that the slice position shift is to be performed, determining, based on the amount of the position shift corresponding to the displacement amount, a second tomographic image at a destination of the slice position shift from a first tomographic image set that is a first plurality of tomographic images including the first tomographic image;
when the identification information specifies that the image capture time shift is to be performed, determining, by an image capture time selector, a third tomographic image from the second tomographic image set that is a second plurality of tomographic images that are identical to the first tomographic image in terms of a target person, examination portions, and a modality but that are different from the first tomographic image set in terms of an image capture time, the third tomographic image selected from the second tomographic image set having a highest correlation with the first tomographic image from the first tomographic image set, the image capture time of the third tomographic image being shifted from an image capture time of the first tomographic image based on an amount of the image capture time shift corresponding to the displacement amount, wherein the difference between the image capture time of the third tomographic image and the image capture time of the first tomographic image is proportional to the displacement amount;
reading out the second tomographic image or the third tomographic image from an image storage device and newly generating display information including a read-out tomographic image; and
determining one or more tomographic images stored in the image storage device are important images;

wherein importance information is added to the one or more tomographic images stored in the image storage device to indicate that the one or more tomographic images are the important images, and wherein when the identification information specifies that the image capture time shift is to be performed and there is a fourth tomographic image added with the importance information indicating that the fourth tomographic image is an important image between the first tomographic image and the third tomographic image, the fourth tomographic image with the importance information is read out from the image storage device for display instead of the third tomographic image determined by the image capture time selector.

* * * * *